*US010099215B2*

United States Patent
Menon et al.

(10) Patent No.: US 10,099,215 B2
(45) Date of Patent: Oct. 16, 2018

(54) MANAGEMENT OF RECHARGER EFFLUENT PH

(71) Applicant: Medtronic, Inc., Minneapolis, MN (US)

(72) Inventors: Kanjimpuredathil Muralikrishna Menon, Bangalore (IN); Ramkumar Jeyachandran, Bangalore (IN); Sukalyan Dutta, Bangalore (IN); Christopher M. Hobot, Tonka Bay, MN (US); David B. Lura, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 328 days.

(21) Appl. No.: 15/143,482

(22) Filed: Apr. 29, 2016

(65) Prior Publication Data

US 2016/0236188 A1 Aug. 18, 2016

Related U.S. Application Data

(63) Continuation-in-part of application No. 14/722,119, filed on May 26, 2015, now Pat. No. 10,052,612, and
(Continued)

(51) Int. Cl.
*B01J 49/75* (2017.01)
*B01J 49/00* (2017.01)
(Continued)

(52) U.S. Cl.
CPC .......... *B01J 49/0078* (2013.01); *A61M 1/169* (2013.01); *A61M 1/1696* (2013.01);
(Continued)

(58) Field of Classification Search
None
See application file for complete search history.

(56) References Cited

U.S. PATENT DOCUMENTS

| 3,840,835 A | 11/1974 | Marantz |
| 3,850,835 A | 11/1974 | Marantz |
| (Continued) | | |

FOREIGN PATENT DOCUMENTS

| CN | 1487853 A | 11/2000 |
| EP | 2446908 | 5/2012 |
| (Continued) | | |

OTHER PUBLICATIONS

European Search Report for App. No. 15812081.6, dated Mar. 8, 2018.
(Continued)

*Primary Examiner* — Richard C Gurtowski
(74) *Attorney, Agent, or Firm* — Kenneth Collier; Roger Hahn

(57) ABSTRACT

Systems and methods for managing effluent from recharging zirconium phosphate and/or zirconium oxide are provided. The systems and methods control the pH of the zirconium phosphate and zirconium oxide effluent to allow for safe disposal. The systems and methods provide for management of the recharger effluent pH while recharging zirconium phosphate and zirconium oxide either independently or concurrently.

20 Claims, 11 Drawing Sheets

Related U.S. Application Data a continuation-in-part of application No. 14/722,068, filed on May 26, 2015, now Pat. No. 9,981,245, said application No. 14/722,119 is a continuation-in-part of application No. 14/261,651, filed on Apr. 25, 2014, now Pat. No. 9,895,477, and a continuation-in-part of application No. 14/642,847, filed on Mar. 10, 2015, now Pat. No. 9,974,896, said application No. 14/722,068 is a continuation-in-part of application No. 14/261,651, filed on Apr. 25, 2014, now Pat. No. 9,895,477, and a continuation-in-part of application No. 14/642,847, filed on Mar. 10, 2015, now Pat. No. 9,974,896.

(60) Provisional application No. 61/941,672, filed on Feb. 19, 2014, provisional application No. 61/909,372, filed on Nov. 26, 2013, provisional application No. 62/016,613, filed on Jun. 24, 2014, provisional application No. 62/077,159, filed on Nov. 7, 2014.

(51) Int. Cl.
| | | |
|---|---|---|
| *B01J 41/10* | (2006.01) | |
| *B01J 39/12* | (2006.01) | |
| *A61M 1/16* | (2006.01) | |
| *B01J 20/34* | (2006.01) | |
| *B01J 20/02* | (2006.01) | |
| *B01J 39/09* | (2017.01) | |
| *B01J 49/53* | (2017.01) | |
| *B01J 49/57* | (2017.01) | |
| *B01J 49/60* | (2017.01) | |

(52) U.S. Cl.
CPC ....... *B01J 20/0211* (2013.01); *B01J 20/3475* (2013.01); *B01J 20/3483* (2013.01); *B01J 39/09* (2017.01); *B01J 39/12* (2013.01); *B01J 41/10* (2013.01); *B01J 49/53* (2017.01); *B01J 49/57* (2017.01); *B01J 49/60* (2017.01); *A61M 2205/3317* (2013.01); *A61M 2205/3324* (2013.01)

(56) References Cited

U.S. PATENT DOCUMENTS

| | | | |
|---|---|---|---|
| 4,192,748 | A | 3/1980 | Hyden |
| 4,687,582 | A | 8/1987 | Dixon |
| 6,579,460 | B1 | 6/2003 | Willis |
| 2002/0112609 | A1 | 8/2002 | Wong |
| 2003/0097086 | A1 | 5/2003 | Gura |
| 2005/0056592 | A1 | 3/2005 | Braunger |
| 2005/0274658 | A1 | 12/2005 | Rosenbaum |
| 2006/0241543 | A1 | 10/2006 | Gura |
| 2008/0011664 | A1 | 1/2008 | Karoor |
| 2008/0241031 | A1 | 10/2008 | Li |
| 2009/0101552 | A1 | 4/2009 | Fulkerson |
| 2009/0282980 | A1 | 11/2009 | Gura |
| 2010/0004588 | A1 | 1/2010 | Yeh |
| 2010/0078387 | A1 | 4/2010 | Wong |
| 2010/0312172 | A1 | 12/2010 | Hoffman |
| 2011/0017665 | A1 | 1/2011 | Updyke |
| 2011/0048949 | A1 | 3/2011 | Ding |
| 2011/0171713 | A1 | 7/2011 | Bluchel |
| 2011/0272352 | A1 | 11/2011 | Braig |
| 2011/0297593 | A1 | 12/2011 | Kelly |
| 2012/0273354 | A1 | 11/2012 | Orhan et al. |
| 2013/0199998 | A1 | 8/2013 | Kelly |
| 2013/0213890 | A1 | 8/2013 | Kelly |
| 2014/0158588 | A1 | 6/2014 | Pudil |
| 2014/0158623 | A1 | 6/2014 | Pudil |
| 2015/0108069 | A1 | 4/2015 | Merchant |
| 2015/0251161 | A1 | 9/2015 | Pudil |
| 2015/0251162 | A1 | 9/2015 | Pudil |
| 2015/0367055 | A1 | 12/2015 | Pudil |

FOREIGN PATENT DOCUMENTS

| | | |
|---|---|---|
| JP | S5070281 A | 6/1975 |
| JP | S51-55193 | 5/1976 |
| JP | S61164562 | 7/1986 |
| JP | 2981573 | 11/1999 |
| JP | 2005511250 | 4/2005 |
| JP | 2007-44602 A | 2/2007 |
| JP | 200744602 | 2/2007 |
| JP | 200744602 A | 2/2007 |
| JP | 2013502987 | 1/2013 |
| JP | 2016-553344 | 5/2018 |
| WO | WO 2011/017215 | 2/2011 |
| WO | WO 2013/019994 | 2/2013 |
| WO | WO 2013-025957 | 2/2013 |
| WO | WO 2013-028809 | 2/2013 |
| WO | WO 2013019179 | 2/2013 |
| WO | 2013101888 | 7/2013 |
| WO | WO 2013/103607 | 7/2013 |
| WO | 2015060914 | 4/2015 |
| WO | 2015199765 | 12/2015 |
| WO | 2015199863 | 12/2015 |
| WO | 2015199864 | 12/2015 |

OTHER PUBLICATIONS

PCT/US2015/032485 Written Opinion dated Oct. 16, 2015.
PCT/US2015/032485 Written Opinion dated May 9, 2016.
European Search Report for EP App. No. 15811326.6, dated Feb. 12, 2018.
European Search Report for EP App. No. 15812413.1, dated Feb. 2, 2018.
PCT/US2016/030319_IPRP.
Search Report in EP App. No. 15752771, dated Nov. 22, 2017.
PCT/US2015/019901 International Preliminary Report on Patentability dated May 27, 2016.
PCT/US2015/019901 International Search Report and Written Opinion dated Jun. 5, 2015.
European Search Report and Supplemental Search Report in European Application No. 14865374.4 dated Jun. 12, 2017.
PCT/US2015/032494 International Preliminary Report on Patentablity dated Dec. 27, 2016.
Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
PCT/US2016/030320 Written Opinion dated Jul. 27, 2016.
Japanese Patent Publication No. S50-70281A.
Office Action in App. No. JP 2016-515476 dated Dec. 26, 2016.
PCT/US2015/032494 Written Opinion dated Nov. 19, 2015.
PCT/US2015/032494 International Search Report dated Nov. 19, 2015.
PCT/US2015/019901 Written Opinion dated May 27, 2016.
PCT/US2015/019901 Written Opinion dated Jun. 5, 2015.
PCT/US2015/032485 International Preliminary Report on Patentability dated May 11, 2016.
PCT/US20115/032485 International Preliminary Report on Patentability dated May 11, 2016.
PCT/US2016/030304 Written Opinion dated Jul. 27, 2016.
PCT/US2016/030312 Written Opinion dated Jul. 28, 2016.
PCT/US2016/030312 International Search Report dated Jul. 28, 2016.
PCT/US2016/030319 International Search Report dated Jul. 27, 2016.
PCT/US2016/030319 Written Opinion dated Jul. 27, 2016.
PCT/US2015/019901 International Search Report dated Jun. 5, 2015.
PCT/US2016/030320 International Search Report dated Jul. 28, 2016.
PCT/US2015/032485 Written Opinion dated Oct. 16, 2016.

(56) References Cited

OTHER PUBLICATIONS

PCT/US2016/030320 International Preliminary Report on Patentability, dated Apr. 20, 2017.
PCT/US2015/032492 Written Opinion dated Nov. 19, 2015.
PCT/US2015/032492 International Search Report dated Nov. 19, 2015.
Office Action in App. No. AU 2015280604 dated Apr. 8, 2016.
Wester et al., A regenerable postassium and phosphate sorbent system to enhance dialysis efficacy and device portability: an in vitro study Nephrol Dial Transplant (2013) 28:2364-2371 Jul. 3, 2013.
John Wm Agar: Review: Understanding sorbent dialysis systems, Nephrology, vol. 15, No. 4, Jun. 1, 2010, pp. 406-411.
PCT/US2016/030304 International Search Report dated Jul. 27, 2016.
PCT/US2016/030320 Written Opinion dated Jul. 28, 2016.
PCT/US2015/032485 International Search Report and Written Opinion dated Oct. 16, 2015.
PCT/US2016/030304_IPRP.
Wheaton, et al., Dowex Ion Exchange Resins-Fundamentals of Ion Exchange; Jun. 2000, pp. 1-9. http://www.dow.com/scripts/litorder.asp? filepath=liquidseps/pdfs/noreg/177-01837.pdf.
John Wm Agar: "Review: Understanding sorbent dialysis systems," Nephrology, vol. 15, No. 4, Jun. 1, 2010, pp. 406-411.
Japanese Patent Publication No. 2007-44602A.

MANAGEMENT OF RECHARGER EFFLUENT PH

FIELD OF THE INVENTION

The invention relates to systems and methods for recharging zirconium phosphate and/or zirconium oxide used in sorbent dialysis. The systems and methods include rechargers, flow paths, related components, and control logic for simultaneously or independently recharging reusable modules containing zirconium phosphate or zirconium oxide and managing effluent pH to allow disposal of fluid without additional treatment.

BACKGROUND

Zirconium phosphate and zirconium oxide are used in sorbent dialysis to remove waste and unwanted solutes from spent dialysate. Generally, zirconium phosphate removes ammonium, potassium, calcium, and magnesium ions from dialysate while the zirconium oxide removes anions such as phosphate or fluoride ions. Both materials are usually packaged together in a cartridge of some type or packed in separate cartridges. Usually, sorbent cartridges are discarded and replaced after use. The discarded sorbent cartridges are broken down and the individual materials separated from each other. Because zirconium phosphate and zirconium oxide are expensive and rechargeable, sorbent re-processors treat the recovered zirconium phosphate and zirconium oxide with chemical solutions. Safe disposal of the chemical waste from solutions used to recharge the materials requires additional steps such as neutralizing the recharging solutions. Conventional methods drive up costs and infrastructure requirements, and increase complexity and waste.

Hence, there is a need for systems and methods that can recharge sorbent materials without the need to separately treat and dispose of the chemical solutions used. There is also a need for a system that can take advantage of solutions necessary to recharge both zirconium oxide and zirconium phosphate to allow for automatic neutralization of the recharging solutions, thus allowing safe disposal without additional treatment. The need extends to coordinating recharging process for both zirconium oxide and zirconium phosphate when only one cartridge is being recharged.

SUMMARY OF THE INVENTION

The first aspect of the invention is drawn to a sorbent recharger. In any embodiment, the sorbent recharger can have at least a first receiving compartment for a first sorbent module; wherein the first receiving compartment has a first sorbent module inlet and a first sorbent module outlet; a first inlet line fluidly connected to the first sorbent module inlet; a first effluent line fluidly connected to the first sorbent module outlet; an disinfectant source, a base source, a water source, and a brine source; wherein at least one of the disinfectant source, base source, water source, and brine source is fluidly connected to the first inlet line; and wherein at least one of the disinfectant source, base source, water source and brine source is fluidly connected to connected to the first effluent line at a common reservoir or a junction with a static mixer at or downstream of the junction.

In any embodiment, the water source, disinfectant source, and brine source can be fluidly connected to the first inlet line; and wherein at least the water source and base source are fluidly connected to the first effluent line.

In any embodiment, the water source, disinfectant source, and base source can be fluidly connected to the first inlet line; and wherein at least the water source and brine source are fluidly connected to the first effluent line.

In any embodiment, the sorbent recharger can include a second receiving compartment for a second reusable sorbent module; the second receiving compartment having a second sorbent module inlet and a second sorbent module outlet; second inlet line fluidly connected to the second sorbent module inlet; a second effluent line fluidly connected to the second sorbent module outlet; and at least one of the disinfectant source, base source, water source, and brine source can be fluidly connected to the second inlet line; and wherein the second effluent line is fluidly connected to the common reservoir or the junction.

In any embodiment, the sorbent recharger can have a conductivity sensor positioned in the first effluent line.

In any embodiment, the sorbent recharger can have a conductivity sensor positioned in at least one of the first effluent line and second effluent line.

In any embodiment, the sorbent recharger can have a first pump in the first inlet line for pumping fluid from the disinfectant source, base source, water source, and/or brine source to the first sorbent module inlet; and a second pump for pumping fluid from the disinfectant source, base source, water source, and/or brine source to the common reservoir or junction.

In any embodiment, the sorbent recharger can have a first pump in the first inlet line for pumping fluid from the disinfectant source, base source, water source, and/or brine source to the first sorbent module inlet; a second pump in the second inlet line for pumping fluid from the disinfectant source, base source, water source, and/or brine source to the second sorbent module inlet; and a controller for controlling the first pump and second pump.

In any embodiment, the controller can be configured to control the first pump to pump fluid from the brine source to the first sorbent module inlet; and to control the second pump to pump fluid from the base source to the common reservoir or junction concurrently.

In any embodiment, the sorbent recharger can have a least one module bypass line, wherein the module bypass line fluidly connects either the first inlet line to the first effluent line; or the second inlet line to the second effluent line.

In any embodiment, the first sorbent module inlet can be fluidly connectable to the first sorbent module outlet and/or the second sorbent module inlet can be fluidly connectable to the second sorbent module outlet.

Any of the features disclosed as being part of the first aspect of the invention can be included in the first aspect of the invention, either alone or in combination.

The second aspect of the invention is drawn a sorbent recharger having at least a first receiving compartment for a first sorbent module; wherein the first receiving compartment has a first sorbent module inlet and a first sorbent module outlet; a first inlet line fluidly connected to the first sorbent module inlet; a first effluent line fluidly connected to the first sorbent module outlet and a common reservoir; and an disinfectant source, a base source, a water source, and a brine source; wherein at least one of the disinfectant source, base source, water source, and brine source is fluidly connected to the first inlet line; and wherein at least one of the disinfectant source, base source, water source and brine source is fluidly connected to the common reservoir.

In any embodiment, the sorbent recharger can have a second receiving compartment for a second reusable sorbent module; the second receiving compartment having a second sorbent module inlet and a second sorbent module outlet; a second inlet line fluidly connected to the second sorbent module inlet; a second effluent line fluidly connected to the second sorbent module outlet; wherein at least one of the disinfectant source, base source, water source, and brine source is fluidly connected to the second inlet line; and wherein the second effluent line is fluidly connected to the common reservoir.

Any of the features disclosed as being part of the second aspect of the invention can be included in the second aspect of the invention, either alone or in combination.

The third aspect of the invention is drawn to a method including the steps of pumping a brine solution through a first reusable sorbent module containing zirconium phosphate; and then pumping a resulting solution to a static mixer or common reservoir; and concurrently pumping a base solution to the static mixer or common reservoir.

In any embodiment, the step of pumping the base solution to the static mixer or common reservoir can include the step of pumping the base solution through a second reusable sorbent module, the second reusable sorbent module containing zirconium oxide.

In any embodiment, the step of pumping the base solution to the static mixer can include the step of pumping the base solution through a module bypass line.

In any embodiment, the method can include pumping fluid from the static mixer to a drain.

In any embodiment, the method can include the step of sensing conductivity or pH in an effluent of the module containing zirconium phosphate; and the step of concurrently pumping a base solution to the static mixer can be carried out when the conductivity sensor senses an increase in conductivity, the pH sensor sensing a decrease in pH, or combinations thereof, in the effluent of the module containing zirconium phosphate.

In any embodiment, the method can include the step of determining a pH in the fluid downstream of the static mixer with a sensor; and pumping the fluid from the static mixer to a drain when the pH of the fluid is between 5 and 9.

Any of the features disclosed as being part of the third aspect of the invention can be included in the second aspect of the invention, either alone or in combination.

The fourth aspect of the invention is drawn to a method including the steps of pumping a base solution through a first reusable sorbent module containing zirconium oxide; and then pumping a resulting solution to a static mixer or common reservoir; and concurrently pumping a brine solution to the static mixer or common reservoir.

In any embodiment, the step of pumping the brine solution to the static mixer or common reservoir can include the step of pumping the brine solution through a second reusable sorbent module, the second reusable sorbent module containing zirconium phosphate.

In any embodiment, the step of pumping the brine solution to the static mixer or common reservoir can include the step of pumping the brine solution through a module bypass line.

In any embodiment, the method can include the step of sensing a conductivity or pH in an effluent of the module containing zirconium oxide; and the step of concurrently pumping a base solution to the static mixer can be carried out when the conductivity sensor senses an increase in conductivity, the pH sensor sensing an increase in pH, or combinations thereof, in the effluent of the module containing zirconium oxide.

Any of the features disclosed as being part of the fourth aspect of the invention can be included in the third aspect of the invention, either alone or in combination.

DETAILED DESCRIPTION OF THE INVENTION

Figure 1:
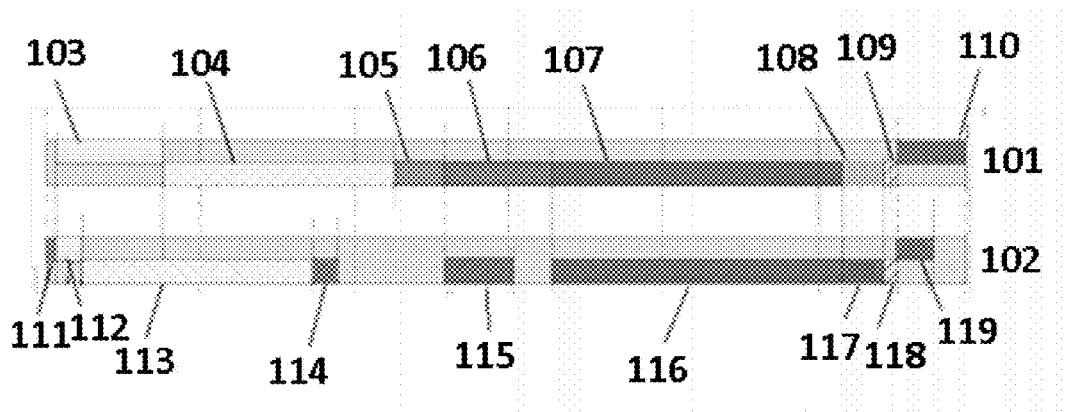
FIG. 1 shows a timeline for concurrent recharging of zirconium oxide and zirconium phosphate.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

A "base solution" is any aqueous solution with a pH of greater than 7.

A "base source" is a fluid or concentrate source from which a basic solution can be obtained.

A "brine solution" refers to any solution comprising acids, bases, and/or salts.

A "brine source" is a fluid or concentrate source from which a brine solution can be obtained. As used herein, a brine solution can refer to any solution comprising acids, bases and/or salts.

A "common reservoir" can be a container for collecting fluid of any type from one or more fluid sources including fluid lines or other reservoirs. The "common reservoir" can, for example, store used or waste fluids.

The term "comprising" includes, but is not limited to, whatever follows the word "comprising." Use of the term indicates the listed elements are required or mandatory but that other elements are optional and may be present.

The term "concurrently" refers to two processes or events taking place at the same time.

The term "conductivity" refers to the inverse of the resistance of a material.

A "conductivity sensor" is a sensor configured to measure the conductivity of a fluid.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "contain," "containing," or "contained" as used herein means to keep a material within a specific place. "Contain" can refer to materials placed within a component, absorbed onto a component, bound to a component, or any other method of keeping the material in a specific place.

The term "control" or "configured to control" refers to the ability of one component to direct the actions of a second component.

A "controller" is any device which monitors and affects the operational conditions of a system. The operational conditions are typically referred to as output variables of the system wherein the output variables can be affected by adjusting certain input variables.

The terms "determining" and "determine" refer to ascertaining a particular state of a system or variable(s).

A "disinfectant source" is a fluid or concentrate source from which a disinfectant solution can be obtained. The disinfectant solution can be an acidic solution, such as a peracetic acid solution, or any other solution capable of disinfecting reusable sorbent modules.

The term "downstream" refers to a position of a first component in a flow path relative to a second component wherein fluid will pass by the second component prior to the first component during normal operation. The first component can be said to be "downstream" of the second component, while the second component is "upstream" of the first component.

A "drain" is a fluid line through which fluids may be disposed.

The term "effluent" refers to fluid exiting a container, compartment, or cartridge.

An "effluent line" is a fluid passageway, tube, or path of any kind into which fluid exiting a container, module, or component will flow.

A "fluid" is a liquid substance optionally having a combination of gas and liquid phases in the fluid. Notably, a liquid, as used herein, can therefore also have a mixture of gas and liquid phases of matter.

The term "fluidly connectable," "fluidly connect," "for fluid connection," and the like, refer to the ability of providing for the passage of fluid, gas, or a combination thereof, from one point to another point. The two points can be within or between any one or more of compartments, modules, systems, components, and rechargers, all of any type. The connection can optionally be disconnected and then reconnected.

A "fluid connector," "fluid connection," and the like describe a connection between two components wherein fluid, gas, or combination thereof, can flow from one component, through a connector or a component for connection, to another component. The connector provides for a fluid connection in its broadest sense and can include any type of tubing, fluid or gas passageway, or conduit between any one or more components of the invention. The connection can optionally be disconnected and then reconnected.

The term "fluid line mixing" refers to mixing fluids at a location or junction wherein flow at the location of junction can, in part, mix one or more fluids.

A "fluid source" is a source from which a fluid or concentrate may be obtained.

An "inlet line" is a fluid line through which fluid entering a container, module, or component will flow.

A "junction" is a location where at least two fluid lines are connected to each other, with or without a valve.

The term "mixing" generally refers to causing one or more fluids from any source to combine together. For example, "mixing" can include laminar or turbulent flow at a location in a fluid line or a junction. Another example of "mixing" can include receiving one or more fluids in a component configured to receive fluids from one or multiple sources and to mix the fluids together in the component. Additionally, mixing can refer to the dissolution of a solid or solids with a fluid, wherein the solid or solids is dissolved in the fluid.

A "module bypass line" refers to a fluid line that provides for movement of fluid between two points without passing through a module.

The term "pH sensor" refers to a device for measuring the pH or hydrogen ion concentration of a fluid.

The term "positioned" or "position" refers to a physical location of a component or structure.

The term "pressure sensor" refers to a device for measuring the pressure of a gas or liquid in a vessel, container, or fluid line.

The term "pump" refers to any device that causes the movement of fluids, gases, or combinations thereof, by applying suction or pressure.

The terms "pumping," "pumped," or to "pump" refer moving a fluid, gas, or combination thereof, with a pump.

A "receiving compartment" is a space within a recharger into which a sorbent module to be recharged is placed.

A "sorbent recharger" is an apparatus designed to recharge at least one sorbent material.

"Recharging" refers to treating a sorbent material to restore the functional capacity of the sorbent material to put the sorbent material back into a condition for reuse or use in a new dialysis session. Sometimes, the total mass, weight and/or amount of "rechargeable" sorbent materials remain the same. Sometimes, the total mass, weight and/or amount of "rechargeable" sorbent materials change. Without being limited to any one theory of invention, the recharging process may involve exchanging ions bound to the sorbent material with different ions, which sometimes may increase or decrease the total mass of the system. However, the total the sorbent material will sometimes be unchanged by the recharging process. Upon a sorbent material undergoing "recharging," the sorbent material can then be said to be "recharged." Recharging of rechargeable sorbent materials is not the same as replenishing of a sorbent material such as urease. Notably, urease is not "recharged," but can be replenished, as defined herein.

A "recharging flow path" is a path through which fluid can travel while recharging sorbent material in a reusable sorbent module.

The term "resulting solution" refers to a solution that is the consequence from one or more prior steps.

The terms "sensing," "sensed" or to "sense" refer to determining one or more parameter or variable.

A "sensor" is a component capable of determining or sensing the states of one or more variables in a system.

A "sorbent cartridge module" or "sorbent module" means a discreet component of a sorbent cartridge. Multiple sorbent cartridge modules can be fitted together to form a sorbent cartridge of two, three, or more sorbent cartridge modules. In some embodiments, a single sorbent cartridge module can contain all of the necessary materials for dialysis. In such cases, the sorbent cartridge module can be a "sorbent cartridge."

A "sorbent module inlet" is a connector through which a fluid, slurry, or aqueous solution can enter a sorbent module.

A "sorbent module outlet" is a connector through which a fluid, slurry, or aqueous solution can exit a sorbent module.

A "static mixer" is a component configured to receive fluids from one or multiple sources and to mix the fluids together. The static mixer may include components that agitate the fluids to further mixing.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "water source" is a fluid source from which water can be obtained.

Recharger Effluent pH Management

FIG. 1 illustrates a non-limiting timeline that uses acidic effluent from the zirconium phosphate recharging process to neutralize the basic effluent from the zirconium oxide recharging process and vice versa. Timeline 101 shows recharging zirconium phosphate and timeline 102 shows recharging zirconium oxide. As illustrated in timeline 101, the zirconium phosphate recharging process can begin by introducing a disinfectant, such as peracetic acid, into the zirconium phosphate module, shown as step 103. The disinfectant can be any disinfectant capable of disinfecting the sorbent modules, including citric acid, bleach, or any other disinfectant known in the art. The time necessary to fill the zirconium phosphate module with the disinfectant can depend on the flow rate of the disinfectant solution and the volume of the zirconium phosphate module. The disinfectant can be delivered to the zirconium phosphate module in step 103 at a flow rate of between 200 and 500 mL/min, which can fill a zirconium phosphate module in a time of between 5-10 minutes. After filling the zirconium phosphate with the disinfectant solution, the disinfectant solution can be held in the zirconium phosphate module to ensure disinfecting of the zirconium phosphate module in step 104. In any embodiment, the disinfectant can be held in the zirconium phosphate module for any length of time sufficient to disinfect the zirconium phosphate module, including between 5 and 20 minutes. The temperature of the disinfectant can be determined with a temperature sensor, and a holding time adjusted as necessary. For example, if the disinfectant temperature is 22° C., the hold time can be 5 minutes. The disinfectant can also be heated to minimize the hold time by heating the disinfectant to room temperature. During the hold time, the disinfectant flow can be stopped or reduced to a low flow condition, such as 5 to 75 ml/min. Sequestering the disinfectant, such as peracetic acid, in the module can build up pressure in the module, requiring periodic venting. To maintain the volume after venting, during which some fluid may leak, the disinfectant can be pumped into the module at a low flow rate during the venting process. Alternatively, the disinfectant flow rate can be set to between 5 and 75 ml/min during the hold time to prevent pressure buildup while maintaining fluid volume in the modules. The disinfectant solution can then be flushed from the zirconium phosphate module in step 105 by pumping water through the zirconium phosphate module. The water can flow through the zirconium phosphate module at a specified rate. A higher flow rate of the water in step 105 will cause a quicker flush time. The water can be pumped through the zirconium phosphate module at a rate of between 100 and 500 mL/min. Depending on the size of the zirconium phosphate module, the zirconium phosphate module can be flushed in one non-limiting example for about 5-10 minutes. Longer or shorter flushing times can be used depending on the need. As described, the system can utilize one or more sensors, such as pH sensors or conductivity sensors in zirconium phosphate effluent lines to sense the pH or conductivity of the effluent and to determine if disinfectant has been fully flushed in step 105. After flushing disinfectant from the zirconium phosphate module in step 105, a brine solution can be pumped through the zirconium phosphate module to recharge the zirconium phosphate module in step 106. The brine solution can be pumped through the zirconium phosphate module in step 106 at any rate. One of skill in the art will understand that a higher flow rate of brine solution may decrease the time necessary to recharge the zirconium phosphate, but may also decrease the efficiency of the process, resulting in additional brine. Conductivity or pH sensors can determine the pH or conductivity of the effluent and to determine if the zirconium phosphate module has been fully filled with brine. The brine flow rate can be set to any flow rate, including between 150 and 250 mL/min. Depending on the size of the zirconium phosphate module, between 5 and 10 minutes may be needed for brine to reach the sensors in the zirconium phosphate effluent line. Once brine has reached sensors in the effluent line, the brine can flow through the zirconium phosphate module in step 107 until recharging is complete.

Recharging time can vary based on the flow rate of the brine solution, the concentration of the brine solution, and the temperature of the brine solution. For example, the brine solution can be heated during the recharging process between 65° C. and 95° C. Recharging of zirconium phosphate can be more efficient at elevated temperatures. Conductivity sensors can determine if step 108 has been completed by sensing the conductivity of the fluid in the zirconium phosphate effluent line. If the conductivity of the effluent matches the conductivity of the brine, then no additional ions from the brine are being exchanged onto the zirconium phosphate, and recharging is complete. For example, steps 108, 109, and 110 represent brine solution being flushed from the zirconium phosphate module with water. Flushing can continue through step 110 until the conductivity sensors in the zirconium phosphate effluent line determine no additional brine is being removed from the zirconium phosphate module.

As depicted in timeline 102 of FIG. 1, zirconium oxide can be recharged concurrently or independently of zirconium phosphate. In step 111, zirconium oxide recharging begins by rinsing the zirconium oxide module with water. The water rinse can flush leftover dialysate bicarbonate or any sodium hydroxide from the flow loop, which may react violently with acid necessary for disinfection. After flushing the zirconium oxide module with water in step 111, disinfectant solution can be delivered to disinfect the module in step 112. The time necessary to fill the zirconium oxide module with disinfectant depends on the size of the zirconium oxide module and the flow rate of the disinfectant. Because less zirconium oxide is needed for dialysis than zirconium phosphate, the zirconium oxide module may be smaller than the zirconium phosphate module, and therefore fill faster in step 112 as compared to the zirconium phosphate module in step 103. Upon filling, the disinfectant can be sequestered in the zirconium oxide module to allow for disinfection in step 113. The disinfectant can be held in the zirconium oxide module for any length of time, including between 5 and 20 minutes. The temperature of the disinfectant can be determined with a temperature sensor, and a hold time adjusted as necessary. For example, if the disinfectant temperature is 22° C., the hold time can be 5 minutes. The disinfectant can also be heated to minimize the necessary hold time. Upon disinfection, the disinfectant can be flushed from the zirconium oxide module in step 114.

In step 115 the base solution flows through the zirconium oxide module to recharge the zirconium oxide. Step 115 continues until a basic solution is detected in the zirconium oxide effluent line. During simultaneous recharging, the basic effluent from the zirconium oxide recharging flow path neutralizes the acidic effluent from the zirconium phosphate recharging flow path. Once a basic effluent is detected in step 115, the zirconium oxide recharging process can be halted until the acid brine is detected in the effluent of the zirconium phosphate module in step 106, which may occur later due to size differences of the zirconium phosphate and zirconium oxide modules. After the acidic effluent is detected in the zirconium phosphate module, shown as step 106, the base can continue to flow through the zirconium oxide module in step 116 concurrently with the brine solution flowing through the zirconium phosphate module. The flow rate of the base solution in step 116 can be any suitable rate. For example, the flow rate of the base solution can be between 30 and 150 mL/min. To ensure neutralization, the flow rate of the base in step 116 can depend on the flow rate of the brine in step 107. As described, the base and effluent are each brought to a point equidistant to a junction between the zirconium phosphate and zirconium oxide effluent lines. Based on the conductivity of each effluent, the pumping is restarted at a ratio of speed that is needed for neutralization. The ratio could be 1:1 or any other ratio. Although described as using a conductivity sensor, the system can alternatively use a pH sensor or a combination of pH and conductivity sensors. A neutralization ratio can be calculated based on the relative pH, buffer capacity, and concentration of the zirconium phosphate effluent and zirconium oxide effluent. For example, a neutralization ratio of 1.5:1 means that 1.5 liters of the zirconium phosphate effluent will be required to fully neutralize one liter of zirconium oxide effluent. The flow rate of the base in step 116 can be set to half the flow rate of the brine solution, allowing full neutralization of both solutions. For example, the flow rate of the base in step 116 can be between 75 and 125 mL/min if the neutralization ratio is 1.5:1 and the brine flow rate is between 150 and 250 mL/min.

After the brine solution is detected in the effluent of the zirconium phosphate and the flushing of the brine begins in step 108, the base solution can pass through the zirconium oxide module, shown as step 117 until the brine is mostly or fully flushed from the zirconium phosphate module, shown as step 109. At this point, the base solution can be flushed from the zirconium oxide module, shown as step 118. After confirming that the base has been flushed from the zirconium oxide module, flushing is completed in step 119.

One of skill in the art will understand that the times and flow rates represented by FIG. 1 can be altered within the scope of the invention. Higher flow rates can cause faster recharging of the modules. Times can be decreased by using more concentrated solutions, but may decrease efficiency. Specified concentrations, flow rates, and times can be set per the needs of the user, taking into account the cost of chemicals and need for fast recharging. The times and flow rates shown in zirconium oxide recharging timeline 102 can be altered to reduce idle time. For example, the flow rate of the base solution in step 115 can be slowed down to reduce the time gap between steps 115 and 116. If a common reservoir is used for the zirconium phosphate and zirconium oxide recharging flow paths either inside or outside of the recharger, the times and flow rates shown in FIG. 1 can be adjusted. Synchronizing the zirconium phosphate timeline 101 with the zirconium oxide timeline 102 is unnecessary because the combined effluent is not directly disposed in a drain.

Figure 2:
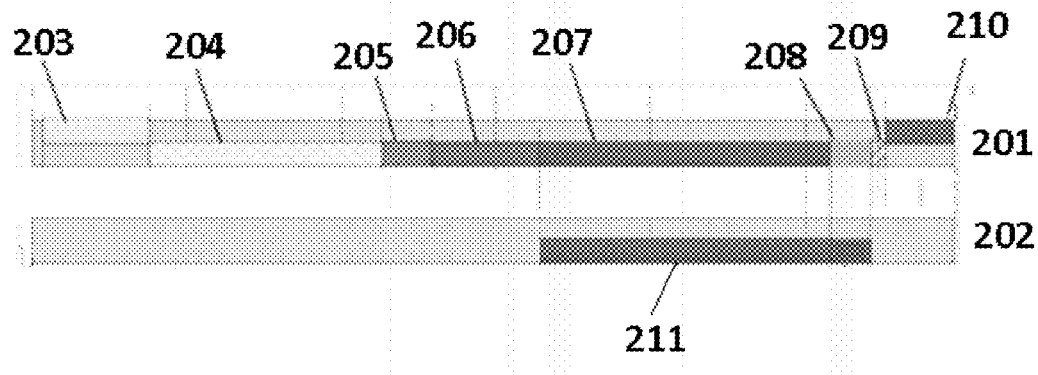
FIG. 2 shows a timeline for independent recharging of zirconium phosphate.

FIG. 2 illustrates a non-limiting example of a timeline that can be used for independent recharging of zirconium phosphate using the dual recharging flow path described herein. Timeline 201 shows recharging zirconium phosphate and timeline 202 shows the process for in-line neutralization of the zirconium phosphate effluent without recharging a zirconium oxide module. As illustrated in timeline 201, the zirconium phosphate recharging process can begin by introducing a disinfectant, such as peracetic acid, into the zirconium phosphate module, shown as step 203. After filling the zirconium oxide with the disinfectant solution, the disinfectant solution can be sequestered in the zirconium oxide module to ensure disinfecting of the zirconium phosphate module in step 204. The disinfectant solution can then be flushed from the zirconium phosphate module in step 205 by pumping water through the zirconium phosphate module at a specified rate. As described, the system can utilize one or more sensors, such as pH sensors or conductivity sensors in the zirconium phosphate effluent lines to determine if disinfectant is fully flushed in step 205. After flushing the disinfectant from the zirconium phosphate module in step 205, brine solution can be pumped through the zirconium phosphate module to recharge the zirconium phosphate module starting in step 206. Once brine has reached the sensors in the effluent line, the brine can flow through the zirconium phosphate module in step 207 until recharging is complete. Concurrently, a base solution can be pumped through the zirconium oxide recharging flow path in step 211 to neutralize the brine solution.

Conductivity sensors can determine if step 208 has been completed by sensing the conductivity of the fluid in the zirconium phosphate effluent line. If the conductivity of the effluent matches the conductivity of the brine, then no additional ions from the brine are being exchanged onto the zirconium phosphate, and recharging is complete. For example, steps 208, 209, and 210 represent brine solution being flushed from the zirconium phosphate module with water. Flushing can continue through step 210 until the conductivity sensors in the zirconium phosphate effluent line determine no additional brine is being removed from the zirconium phosphate module. Once the conductivity sensors determine that the pH of the zirconium phosphate effluent is safe for disposal without additional treatment, the base solution in the zirconium oxide recharging flow path is stopped. The fluid flow rates and concentrations used in the process illustrated in FIG. 2 can be the same as the fluid flow rates and concentrations described with reference to FIG. 1.

Figure 3:
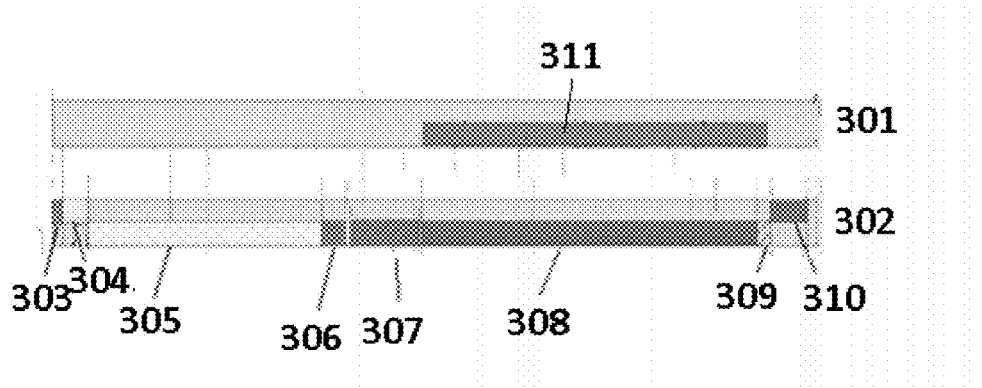
FIG. 3 shows a timeline for independent recharging of zirconium oxide.

FIG. 3 shows a timeline for independently recharging zirconium oxide. Timeline 302 shows the recharging of zirconium oxide and timeline 301 shows using the zirconium phosphate recharging flow path for in-line neutralization of the zirconium oxide effluent. In step 303, zirconium oxide recharging begins by rinsing the zirconium oxide module with water to flush leftover dialysate bicarbonate, which may react violently with acid necessary for disinfection. After flushing the zirconium oxide module with water in step 303, disinfectant solution can be delivered to disinfect the module in step 304. Upon filling, the disinfectant can be sequestered in the zirconium oxide module to allow for disinfection in step 305. Upon disinfection, the disinfectant can be flushed from the zirconium oxide module in step 306.

In step 307 the base solution flows through the zirconium oxide module to recharge the zirconium oxide. Step 307 continues until a basic solution is detected in the zirconium oxide effluent line. Once the basic solution is detected in the zirconium oxide effluent line, brine is concurrently pumped through the zirconium phosphate recharging flow path for in-line neutralization of the basic zirconium oxide effluent in step 311. The base solution continues to flow through the zirconium oxide module until recharging is complete in step 308. After recharging the zirconium oxide in step 308, the basic solution can be flushed in steps 309 and 310. Conductivity sensors in the zirconium oxide effluent line determine when the basic solution is fully flushed, at which point the brine solution in step 311 can be stopped. The process illustrated in FIG. 3 can use the same flow rates and concentrations as described with respect to FIG. 1.

Figure 4:
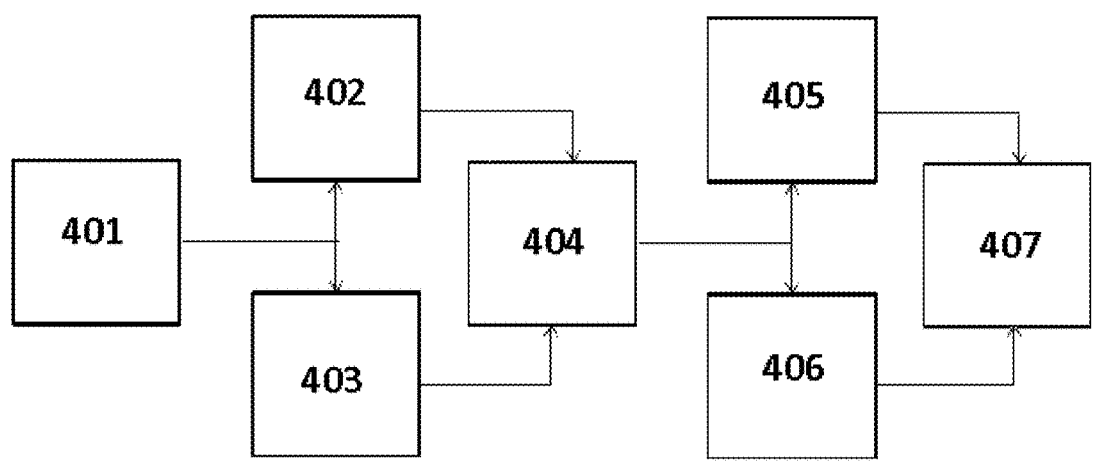
FIG. 4 is a flow chart illustrating the steps for in-line neutralization of the recharger effluent.

FIG. 4 provides a flow chart illustrating the steps for in-line neutralization of the zirconium phosphate recharging effluent and zirconium oxide recharging effluent. In step 401, the zirconium oxide module can be flushed with water, and each of the zirconium oxide and zirconium phosphate modules can be filled with disinfectant for disinfection, followed by flushing of the disinfectant solution. After disinfection and flushing, the zirconium phosphate module can be filled with brine in step 402 and the zirconium oxide module can be filled with a base in step 403. The conductivity or pH of the effluent of the zirconium oxide module and zirconium phosphate module can be sensed by a conductivity or pH sensor in step 404. Steps 402 and 403 are continued until the system senses both brine in the zirconium phosphate effluent and base in the zirconium phosphate effluent in step 404. If the system detects only base in the zirconium oxide effluent but not brine in the zirconium phosphate effluent, step 403 can be halted until the brine is detected in the zirconium phosphate effluent. After detecting both brine in the zirconium phosphate effluent and base in the zirconium oxide effluent in step 404, the recharging process can continue with pumping brine through the zirconium phosphate module in step 405 and pumping base through the zirconium oxide module in step 406. The conductivities of the zirconium phosphate and zirconium oxide effluents can be sensed in step 407, and steps 405 and 406 continued until no change is detected in the conductivity of each of the effluents in step 407. After the system determines there is no change in the effluent conductivity of each of the modules in step 407, recharging is complete and the modules can be rinsed with water and reused. At any point during step 407 a pH sensor or conductivity sensor can sense the combined effluent of the zirconium phosphate and zirconium oxide modules to ensure that the combined effluent has a pH safe for disposal. In any embodiment, the system can ensure that the combined effluent has a pH of between 5-9. If the pH is outside of this range, the system can prevent the disposal of the combined effluent.

In any embodiment, the system can include a controller for controlling the pumps and valves described. The controller can receive data from the conductivity or pH sensors and control the pumps and valves to carry out the processes described with in-line neutralization of the recharging effluent.

The zirconium oxide and zirconium phosphate sorbent modules can be recharged and reused any number of times. Alternatively, the sorbent modules may have a defined useful life, including a maximum number of recharge and reuse cycles. When a sorbent module reaches the end of the sorbent module's useful life, the sorbent module can be recycled or disposed of. A disinfection only cycle can disinfect the sorbent modules for safe disposal and/or recycling at the end of the sorbent module's useful life. In a disinfection only cycle, the disinfectant can be pumped into the sorbent module as described but the other recharge solutions would not be used. After disinfection, and optionally rinsing of the sorbent module, the sorbent module can be disposed or recycled safely.

Figure 5A:
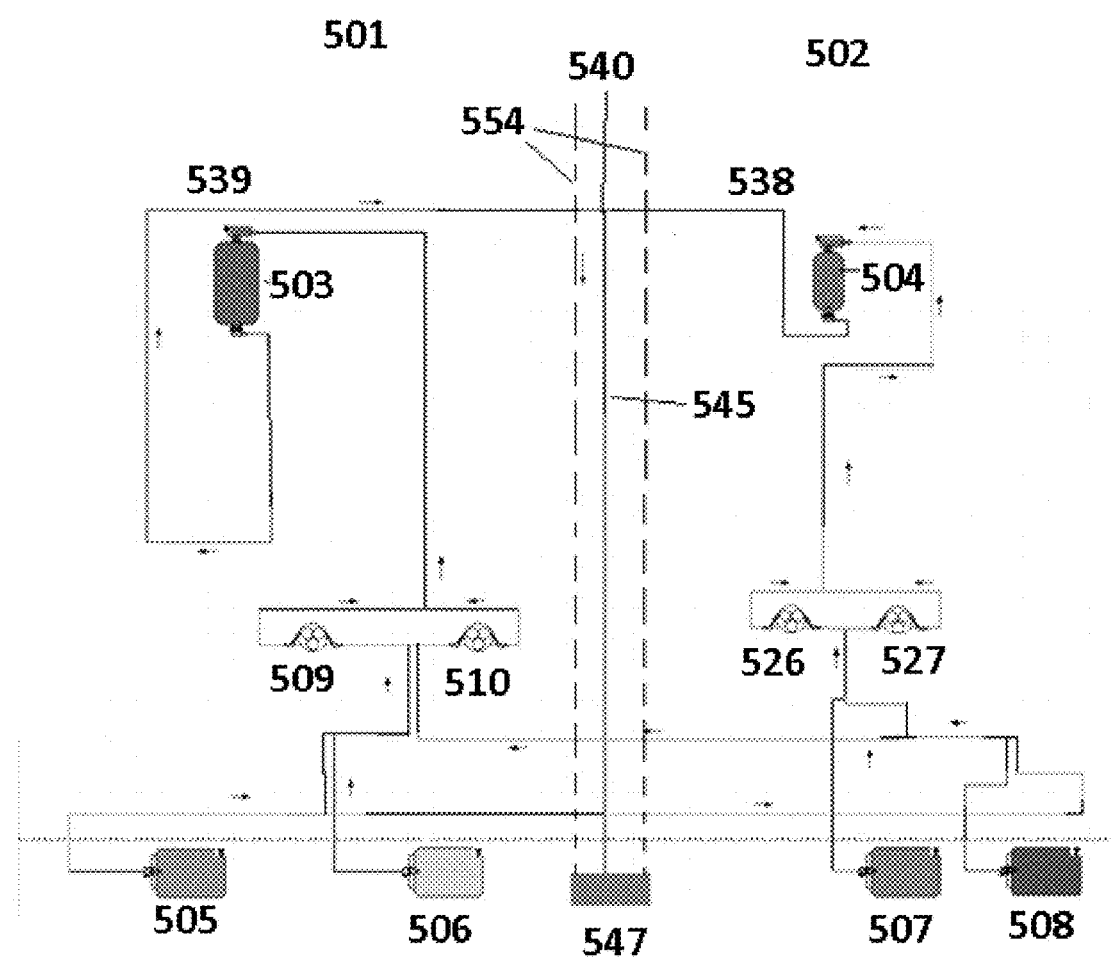
FIG. 5A shows a recharging flow path for recharging zirconium phosphate and zirconium oxide.
Figure 5B:
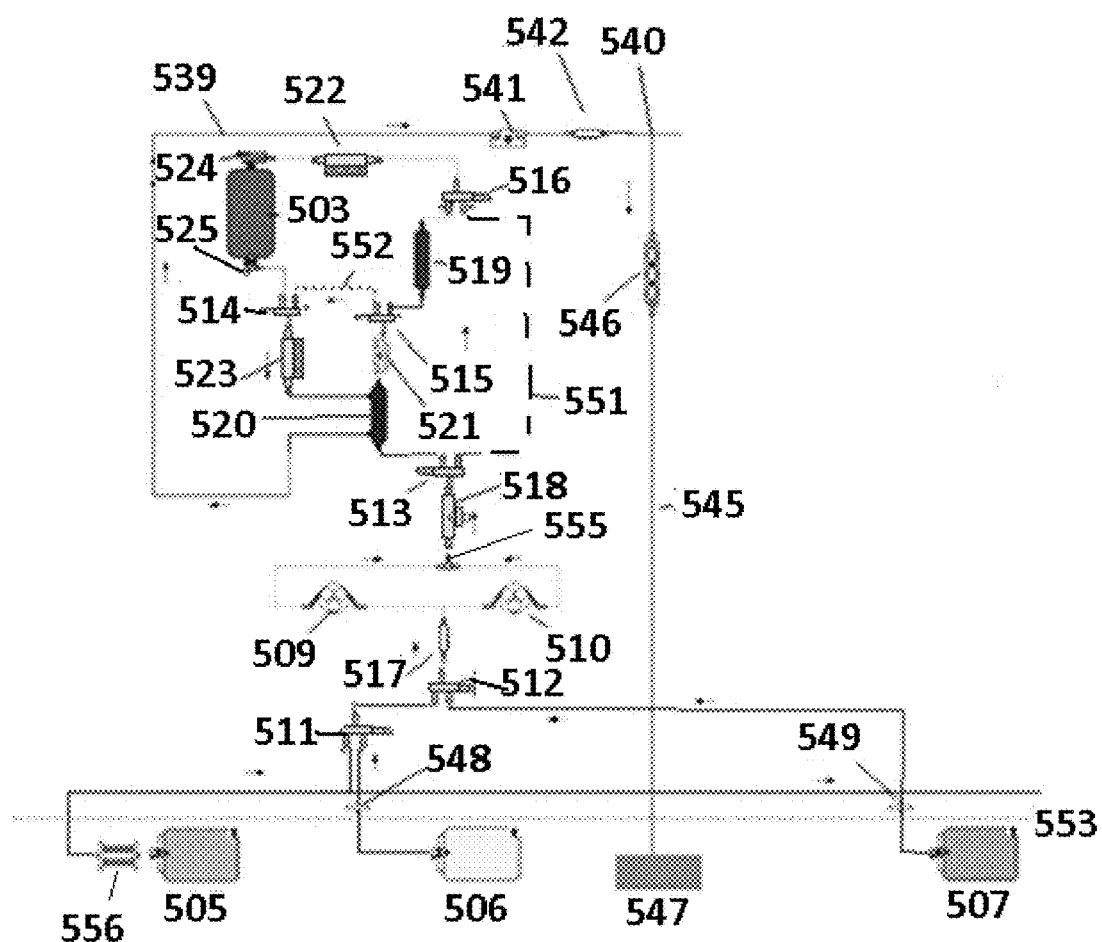
FIG. 5B shows a recharging flow path for recharging zirconium phosphate and is an exploded left side of FIG. 5A.
Figure 5C:
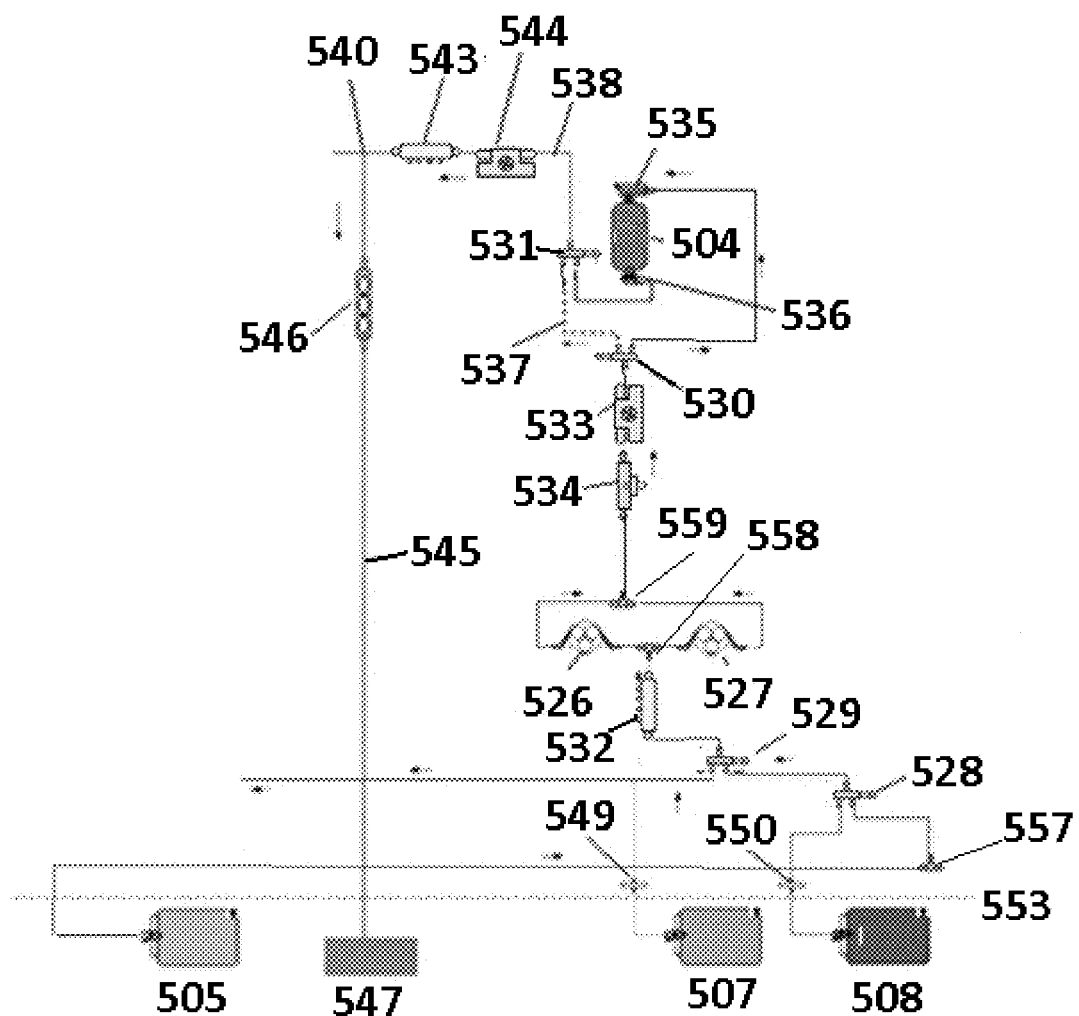
FIG. 5C shows a recharging flow path for recharging zirconium oxide and is an exploded right side of FIG. 5A.

To recharge the sorbent materials, fluids from fluid sources are passed through the sorbent modules. The flow paths of the invention can be arranged as shown in FIGS. 5A-C. FIG. 5A is a generalized view of a recharging flow path, with details shown in FIGS. 5B and 5C. The recharging flow path can be divided into a zirconium phosphate recharging flow path 501 containing the zirconium phosphate module 503 and a zirconium oxide recharging flow path 502 containing zirconium oxide module 504. Details of the zirconium phosphate recharging flow path 501 on the zirconium phosphate side of line 554 are illustrated in FIG. 5B, while details of the zirconium oxide recharging flow path 502 on the zirconium oxide side of line 554 are illustrated in FIG. 5C. Although a dual cartridge recharger system is shown, single, two or more multiple cartridge recharger systems are envisioned. Any one of the recharger cartridge systems can be linked together to share resources for recharging the sorbent cartridge and can be adapted for large scale use. Similarly, the linked rechargers can be scaled down as demand for recharging decreases. The modular recharging set-up having more or less rechargers based on demand can be advantageously used where required.

In FIG. 5A, a zirconium phosphate recharging flow path 501 and a zirconium oxide recharging flow path 502 have a water source 505, a brine source 506, a disinfectant source 507, and a base source 508. The brine source 506, disinfectant source 507, and/or base source 508 can be a column containing a dry bed of the brine, acid, and/or base components. Alternatively, a powdered source of the brine, acid, and/or base components can be used. The dry bed or powdered source can be dissolved with an aqueous solution. A static mixer (not shown) can mix the single line coming through the column prior to entering the zirconium phosphate module 503 or zirconium oxide module 504. Recharging the zirconium phosphate in a zirconium phosphate module 503 requires water, brine, and disinfectant. The water source 505, the brine source 506, and the disinfectant source 507 are fluidly connected to the zirconium phosphate recharging flow path 501. Similarly, recharging zirconium oxide module 504 in zirconium oxide recharging flow path 502 requires water, base, and disinfectant. The water source 505, the disinfectant source 507, and the base source 508 are fluidly connected to the zirconium oxide recharging flow path 502. The zirconium phosphate recharging flow path 501 and zirconium oxide recharging flow path 502 can be operated simultaneously or independently. Disinfectant source 507 can contain any type of disinfectant compatible with zirconium phosphate and zirconium oxide that is capable of disinfecting the reusable sorbent modules. In any embodiment, the disinfectant source 507 can contain peracetic acid. In any embodiment, the peracetic acid can be a solution of between 0.5% and 2% peracetic acid in water. The brine source 506 can have an acid, a base, and a sodium salt.

During zirconium phosphate recharging, potassium, calcium, magnesium, and ammonium ions bound to the zirconium phosphate must be replaced by hydrogen and sodium ions. The final ratio of hydrogen to sodium ions on the recharged zirconium phosphate can be determined by the pH, buffer capacity, and sodium concentration of the brine solution used in the recharging process. The brine source 506 can be a mixture of sodium chloride, sodium acetate, and acetic acid. In one non-limiting brine solution, the sodium chloride concentration can be between 2.5M and 4.9M, the sodium acetate concentration can be between 0.3M and 1.1M, and acetic acid concentration can be between 0.2M and 0.8M. The water source 505 can contain any type of water, including deionized water. To recharge the zirconium phosphate in the zirconium phosphate module 503, the disinfectant from disinfectant source 507 can flow to the zirconium phosphate module 503 to disinfect the zirconium phosphate module 503. Fluid from the disinfectant source 507 can flow to valve 512 in the zirconium phosphate recharging flow path 501. Zirconium phosphate pumps 509 and 510 provide a driving force to pump the fluid through the zirconium phosphate recharging flow path 501. Use of two or more separate pumps can reduce wear on the pumps. Correspondingly, smaller pumps can be used. The two or more pumps can provide in-line mixing and intermittent pumping so at any given time, a single pump can pump fluid through the zirconium phosphate recharging flow path 501. The two pumps can be used simultaneously or independently. The two or more pumps can provide fluid line mixing for one or more separate fluid streams when used simultaneously. The two or more pumps can operate asynchronously but used concurrently. For example, a first pump can operate for a time and a second pump remain off, then the first pump shut off with the second pump turning on. Multiple pumps at various timed pumping stages are envisioned as described herein. One of skill in the art will understand that a single zirconium phosphate pump can also accomplish the described pump functions.

Zirconium phosphate pumps 509 and 510 can pump fluid from disinfectant source 507 through valve 512 and valve 513. Fluid can be pumped through three-way junction 555 to valve 516 and into zirconium phosphate module 503 through zirconium phosphate sorbent module inlet 524. The illustrated junctions combine the inlet chemicals or water pumped by the two pumps such that higher flow rates can be achieved. During filling, fluid inside zirconium phosphate module 503 can be forced through zirconium phosphate sorbent module outlet 525 and into zirconium phosphate module effluent line 539. The disinfectant can be sequestered in the zirconium phosphate module 503 to ensure disinfection. Heater 519 upstream of the zirconium phosphate module 503 can heat the disinfectant because disinfection can become more efficient at elevated temperatures. After disinfection, zirconium phosphate module 503 can be rinsed using water from water source 505. Zirconium phosphate pumps 509 and 510 can pump water from water source 505 through valves 511 and 512 to valve 513. The water can then be pumped through valves 515 and 516 through the zirconium phosphate module 503 through zirconium phosphate sorbent module inlet 524, out zirconium phosphate sorbent module outlet 525 and into zirconium phosphate module effluent line 539. Water can be pumped through the zirconium phosphate module 503 until all of the disinfectant is removed.

Fluid from brine source 506 can be pumped through the zirconium phosphate module 503 to load the zirconium phosphate module 503 with the proper ratio of sodium and hydrogen ions. Zirconium phosphate pumps 509 and 510 can pump fluid from brine source 506 to valve 511. The brine can follow the same pathway as the water through zirconium phosphate module 503 and into zirconium phosphate module effluent line 539. Heater 519 upstream of the zirconium phosphate module 503 can heat brine because recharging can become more efficient at elevated temperatures. Heat exchanger 520 can lessen the load on heater 519. One or more heat exchangers and one or more heaters can be used. The heat exchanger 520 can be fluidly connected to zirconium phosphate module effluent line 539 and to zirconium phosphate sorbent module inlet 524 upstream of heater 519. The heated fluid exiting the zirconium phosphate module 503 in zirconium phosphate module effluent line 539 can heat the incoming brine solution in heat exchanger 520. The heat exchanger 520 can have at least a first chamber and a second chamber. Fluid in the zirconium phosphate inlet lines can pass through the first chamber of the heat exchanger 520, and fluid in the zirconium phosphate effluent line 539 can pass through the second chamber of the heat exchanger 520. The increased temperature of the zirconium phosphate effluent in the second chamber can heat the fluid in the zirconium phosphate inlet lines in the first chamber. The zirconium phosphate module 503 can be rinsed again by pumping water through the zirconium phosphate module 503. A static mixer (not shown) can be positioned upstream of the zirconium phosphate module 503 and mix the solutions prior to entering the zirconium phosphate module 503.

Various sensors can be used in the zirconium phosphate module recharging flow path 501 to ensure proper concentrations and temperatures as shown in FIG. 5B. For example, conductivity sensor 517 can ensure that the incoming water contains no level of ions that may interfere with the recharging process, and that the brine solution and disinfectant solution are at a desired concentration. Conductivity sensor 517 can also ensure that sufficient rinsing has occurred to remove brine and disinfectant solution. Pressure sensor 518 can monitor pressure in the zirconium phosphate inlet lines to ensure there are no occlusions or leaks and that the inlet pressures are in an acceptable range. Temperature sensor 522 can ensure that the brine solution is at the proper temperature before entering zirconium phosphate module 503 and to control heater 519. Temperature sensor 523 can be placed in zirconium phosphate module effluent line 539 to monitor the temperature of the effluent which can be controlled by heat exchanger 520 and heater 519. A flow sensor 521 can monitor the flow rates of the fluids in the zirconium phosphate recharging flow path 501 and control zirconium phosphate pumps 509 and 510. One of skill in the art will understand that alternative arrangements of sensors can be used in FIG. 5B and that one or more additional sensors can be added. Further, the sensors can be placed at any appropriate position in the zirconium phosphate recharging flow path 501 to determine fluid parameters at various locations throughout the zirconium phosphate recharging flow path 501.

Zirconium phosphate module bypass line 552 fluidly connects valve 515 to valve 514 in the zirconium phosphate effluent line 539. Valves 515 and 516 can be controlled to direct fluid through the zirconium phosphate module bypass line 552 and into zirconium phosphate effluent line 539. The dual flow path aspect of the recharging flow path depicted in FIG. 5A can neutralize the effluent from both the zirconium phosphate module 503 and zirconium oxide module 504 by mixing the acidic effluent from the zirconium phosphate module 503 with the basic effluent from zirconium oxide module 504. If only zirconium oxide module 504 is being recharged using the flow path of FIG. 5C, the zirconium phosphate module bypass line 552 can be utilized to direct fluid from the brine source 506 to the zirconium phosphate effluent line 539 to neutralize the zirconium oxide effluent without the need to simultaneously recharge a zirconium phosphate module 503. Alternatively, zirconium phosphate sorbent module inlet 524 can directly connect to zirconium phosphate sorbent module outlet 525. The zirconium phosphate recharging flow path 501 can include a rinse loop 551 to fluidly connect valve 513 upstream of the heater 519 and heat exchanger 520 to valve 516, bypassing heater 519 and heat exchanger 520. The rinse loop 551 can rinse brine solution from the zirconium phosphate module 503. By bypassing heater 519 and heat exchanger 520 through rinse loop 551, the zirconium phosphate module 503 can be cooled faster.

To recharge the zirconium oxide module 504, disinfectant from disinfectant source 507 can be first pumped to the zirconium oxide module 504 to disinfect the zirconium oxide module 504. Fluid from the disinfectant source 507 can be pumped to valve 529 in the zirconium oxide recharging flow path 502. Zirconium oxide pumps 526 and 527 can pump fluid through the zirconium oxide recharging flow path 502. As described, a single zirconium oxide pump is contemplated as an alternative to the dual pump system in FIG. 5. Also, two or more zirconium oxide pumps are contemplated. The two or more zirconium oxide pumps can provide fluid line mixing of one or more separate fluid streams when used simultaneously. The two or more pumps can be asynchronous but used concurrently. For example, a first pump can operate for a time and a second pump remain off, then the first pump shut off with the second pump turning on. Multiple pumps at various timed pumping stages are envisioned as described herein. Zirconium oxide pumps 526 and 527 pump fluid from disinfectant source 507 through valve 529 to valve 530. The fluid flows to the zirconium oxide module 504 through zirconium oxide sorbent module inlet 535. During filling, fluid inside zirconium oxide module 504 can flow through zirconium oxide sorbent module outlet 536 and into zirconium oxide module effluent line 538. The disinfectant can be sequestered in zirconium oxide module 504 to ensure disinfection. The zirconium oxide module 504 can then be flushed with water from water source 505 after disinfection is completed. Zirconium oxide pumps 526 and 527 can pump water from water source 505 through valves 528 and 529 and junction 557 to valve 530. The fluid passes through junctions 558 and 559 to reach valve 530. The water can then be pumped to zirconium oxide module 504 through zirconium oxide module inlet 535 and out zirconium oxide sorbent module outlet 536 and into zirconium oxide module effluent line 538. The zirconium oxide module 504 can be flushed with any volume of water required to ensure that the disinfectant is completely removed.

In FIG. 5C, zirconium oxide pumps 526 and 527 can pump fluid from base source 508 through valve 528 to zirconium oxide module 504. The base source 508 can contain hydroxide ions to recharge zirconium oxide module 504. The hydroxide ions can flow through zirconium oxide module 504 and into zirconium oxide module effluent line 538. The base source 508 can be any suitable basic solution capable of replacing phosphate and other anions bound to the zirconium oxide with hydroxide ions. The hydroxide base can be any suitable base such as sodium hydroxide. One non-limiting example is sodium hydroxide having a concentration between 0.5M and 2.0M. Another non-limiting example is sodium hydroxide having a concentration at 90% or greater than 2% of the concentration of the recharging solution. A final rinse of the zirconium oxide module 504 can be performed by pumping water through the zirconium oxide recharging flow path 502 and zirconium oxide module 504. Zirconium oxide recharging flow path 502 can also have a zirconium oxide module bypass line 537 fluidly connecting valve 530 in the zirconium oxide inlet line to valve 531 in the zirconium oxide effluent line 538. Valves 530 and 531 can direct fluid through the zirconium oxide module bypass line 537 and into zirconium oxide effluent line 538. Zirconium oxide module bypass line 537 can convey fluid directly from the base source 508 to the zirconium oxide effluent line 538 to neutralize the zirconium phosphate effluent without the need to simultaneously recharge a zirconium oxide module 504. Alternatively, zirconium oxide sorbent module inlet 535 can be fluidly connected to zirconium oxide sorbent module outlet 536. Multiple sensors can be included in the zirconium oxide recharging flow path 502 to monitor fluid concentration. For example, conductivity sensor 532 can monitor concentrations of the zirconium oxide recharging fluid; pressure sensor 534 can monitor pressure in the zirconium oxide inlet line and to detect leaks or occlusions. Flow sensor 533 can determine the flow rate of the fluid through the zirconium oxide inlet line and be used to control zirconium oxide pumps 526 and 527. A static mixer (not shown) can be positioned upstream of the zirconium oxide module 504 and mix solutions prior to entering the zirconium oxide module 504. A heater and heat exchanger (not shown) can be positioned in the zirconium oxide recharging flow path 502 to heat fluids prior to entering zirconium oxide module 504. Heating fluid in the zirconium oxide recharging flow path 502 can reduce recharging times and allow disinfection with a base solution, such as sodium hydroxide. Heating the fluid also allows for reduced disinfection time with a disinfectant source. A zirconium oxide rinse loop (not shown) can also be included to bypass the heater and heat exchanger during flushing.

Effluent from zirconium phosphate recharging flow path 501 can neutralize, either completely or in part, the effluent from zirconium oxide recharging flow path 502, and vice versa. Zirconium phosphate effluent line 539 can be fluidly connected to zirconium oxide effluent line 538 at an effluent line junction 540 joining drain line 545, which fluidly connects to drain 547. Static mixer 546 can be used at or downstream of the effluent line junction 540 to mix zirconium phosphate effluent with zirconium oxide effluent.

Zirconium phosphate effluent line 539 and zirconium oxide effluent line 538 can be connected to a common reservoir for storage and disposal of the combined effluent. The common reservoir receives and collects the zirconium phosphate and zirconium oxide effluents together. The collected effluents can be drained after appropriate volumes of each effluent have been added to achieve neutralization. A common reservoir can allow for neutralization of the zirconium phosphate and zirconium oxide effluents without synchronizing the recharging processes. A single common reservoir can be sized to support multiple recharge stations.

Alternatively, the two fluid streams may be mixed through fluid line mixing at the effluent line junction 540. Flow sensor 541 and conductivity sensor 542 can be placed in zirconium phosphate effluent line 539 to measure the flow rate and composition of the zirconium phosphate effluent. Flow sensor 544 and conductivity sensor 543 can be positioned in the zirconium oxide effluent line 538 to measure the flow rate and composition of the zirconium oxide effluent. Data from flow sensors 541 and 544 and conductivity sensors 542 and 543 can determine if the combined effluent in drain line 545 is safe for disposal into a drain. One non-limiting example of safe is an effluent having a pH in the range of 5-9. Either zirconium phosphate effluent line 539 or zirconium oxide effluent line 538 can be connected simultaneously or independently to a waste reservoir (not shown) for disposal. Additional pH or conductivity sensors can be positioned downstream of the static mixer 546 to monitor and ensure safe disposal. Drain line 545 can also be connected to a common waste reservoir for storage and disposal of effluent. The common reservoir receives and collects the zirconium phosphate and zirconium oxide effluents together. The collected effluents can be drained after appropriate volumes of each effluent have been added to achieve neutralization. A common waste reservoir advantageously allows for neutralization of the zirconium phosphate and zirconium oxide effluents without synchronizing the recharging processes. Static mixer 546 is unnecessary when a common reservoir is used.

Brine source 506, disinfectant source 507, and base source 508 can have filter 548, filter 549, and filter 550, respectively to remove particulate matter. The one or more filters can remove particulate matter before fluid enters the zirconium oxide recharging flow path 502 or zirconium phosphate recharging flow path 501. Water source 505 can have microbial filter 556 to remove microbes from the water before entering the flow paths. In FIG. 5C, the dashed line 553 represents a recharger housing. The fluid sources can be external to the recharger housing and fluidly connected to the lines located inside of the recharger housing. Alternatively, the fluid sources described can instead be housed within the recharger.

During recharging, fluid can be passed through the zirconium phosphate module 503 and/or the zirconium oxide module 504 opposite to a flow direction used during dialysis. For example, zirconium phosphate sorbent module inlet 524 can be used as the zirconium phosphate sorbent module outlet during dialysis, and zirconium phosphate sorbent module outlet 525 can be used as the zirconium phosphate sorbent module inlet during dialysis in FIG. 5B. Similarly, zirconium oxide sorbent module inlet 535 can be used as the zirconium phosphate sorbent module outlet during dialysis, and zirconium oxide sorbent module outlet 536 can be used as the zirconium phosphate sorbent module inlet during dialysis. Pumping the recharging fluid through the modules in the opposite direction relative to dialysis can improve the efficiency of the recharging process.

The zirconium phosphate recharging flow path 501 or zirconium oxide recharging flow path 502 can independently recharge zirconium phosphate or zirconium oxide. For example, a single flow path fluidly connecting zirconium phosphate module 503 of FIG. 5B via valve 512 and valve 513 to each of the water source 505, brine source 506, and disinfectant source 507 can independently recharge the zirconium phosphate module 503. Similarly, a single flow path fluidly connecting zirconium oxide module 504 of FIG. 5C via valve 528 and valve 529 to each of the water source 505, disinfectant source 507, and base source 508 can independently recharge the zirconium oxide module 504.

The water source 505, brine source 506, disinfectant source 507, and base source 508 can recharge one or more reusable sorbent module of various sizes. The amount of water, brine, disinfectant, and base depends on the concentration of each of the recharging solutions, the size of the reusable sorbent modules, the amount of cations/anions removed, and the flow rate used to pass the solutions through the reusable modules. The amount of brine solution required can depend on the temperature to which the brine solution is heated. For example, a brine solution having between 2.5M and 4.9M sodium chloride, between 0.3M and 1.1M sodium acetate, and between 0.2M and 0.8M acetic acid at between 70° C. and 90° C. requires between 4.2-6.2 L of brine to recharge a zirconium phosphate module containing between 2 kg and 3.2 kg of zirconium phosphate loaded with 2 to 3 moles of ammonium, calcium, magnesium and potassium. The brine solution should have a volume of at least between 4.2 and 6.2 L and delivered at a flow rate of between 100 and 300 mL/min. A single brine source can be connected to multiple rechargers, or can recharge multiple zirconium phosphate modules in a single recharger. The brine source can have a significantly larger volume from 1-100× or greater to ensure that the brine source toned not be refilled each time a zirconium phosphate is recharged. For a zirconium oxide module having between 220 and 340 g of zirconium oxide loaded with 200 mmols of phosphate, a base source having between 0.5 and 2.0M sodium hydroxide and a flow rate between 30 and 150 mL/min requires between 1 and 4 L of base. The base source can be at least between 1 and 4 L in volume. For recharging multiple zirconium oxide modules, a larger base source can be used.

Figure 6A:
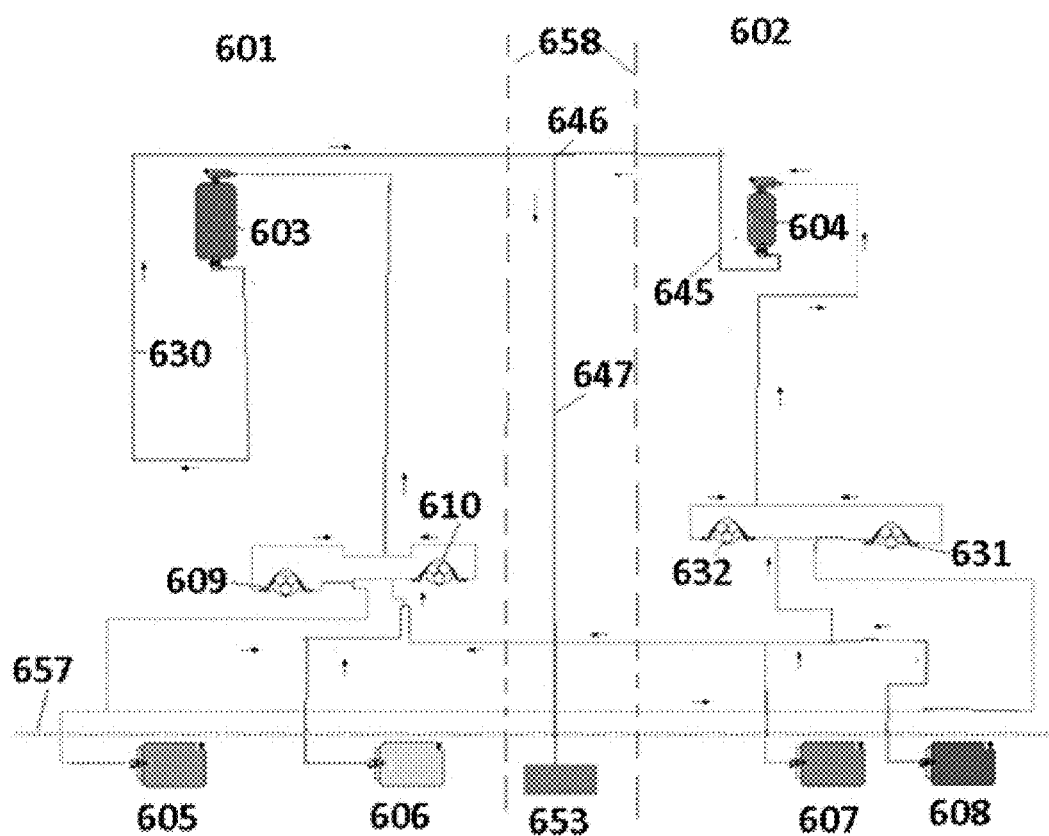
FIG. 6A shows a recharging flow path for recharging zirconium phosphate and zirconium oxide with in-line mixing of recharging solutions.
Figure 6B:
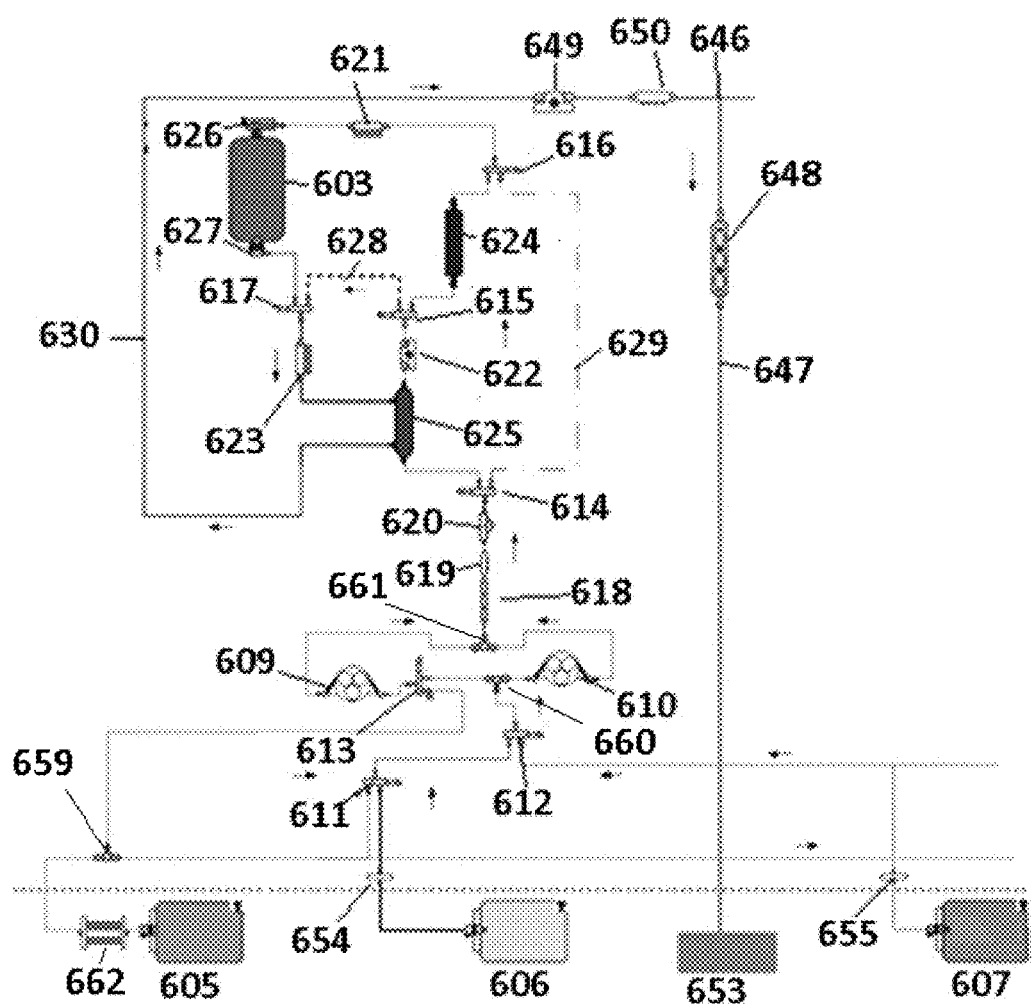
FIG. 6B shows a recharging flow path for recharging zirconium phosphate with in-line mixing of recharging solutions and is an exploded right side of FIG. 6A.
Figure 6C:
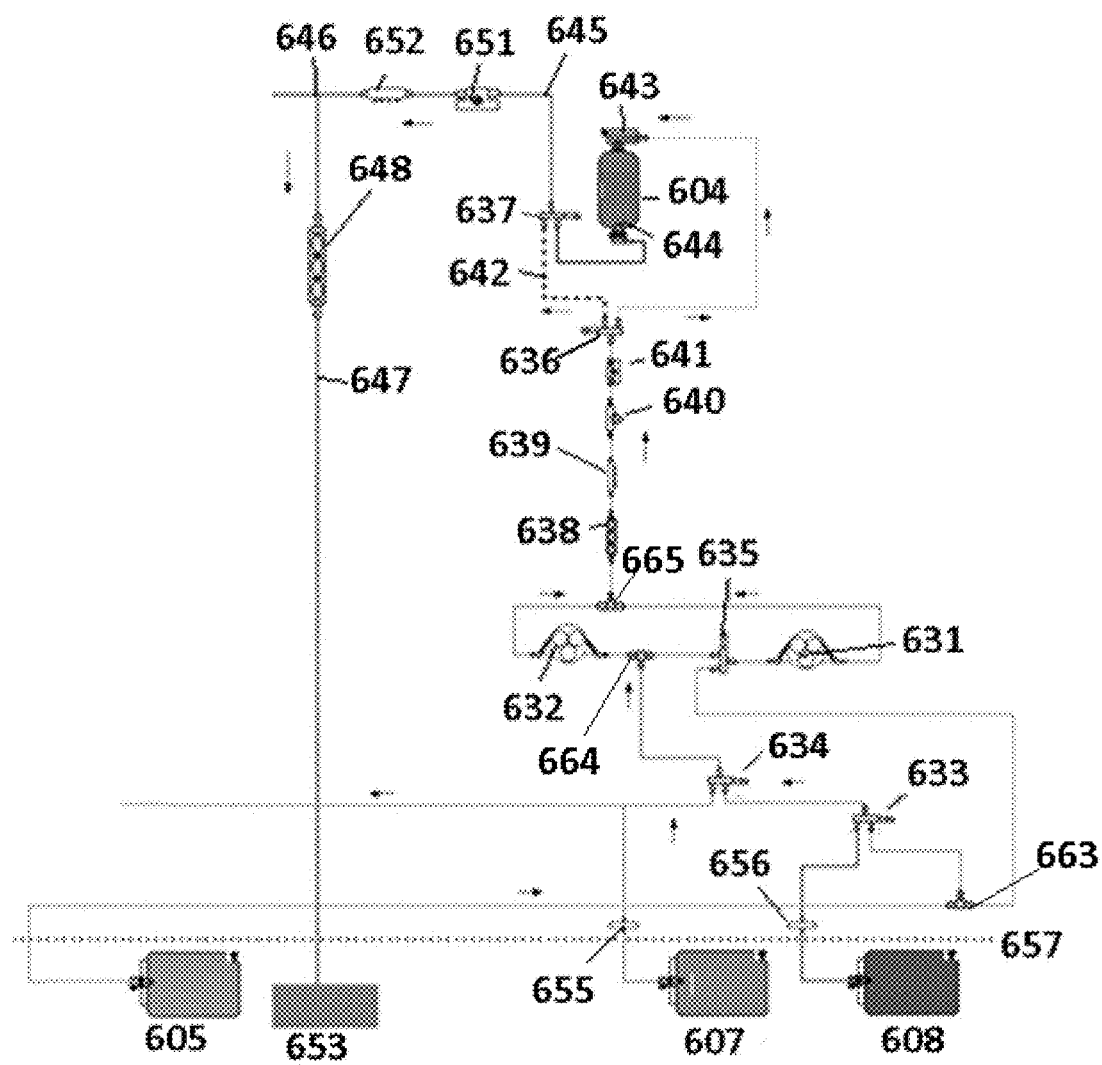
FIG. 6C shows a recharging flow path for recharging zirconium oxide with in-line mixing of recharging solutions and is an exploded left side of FIG. 6A.

FIG. 6A is a generalized view of a recharging flow path having a zirconium phosphate recharging flow path 601 containing a zirconium phosphate module 603 and a zirconium oxide recharging flow path 602 containing a zirconium oxide module 604. FIG. 6B illustrates a detailed view of zirconium phosphate recharging flow path 601 on the zirconium phosphate side of line 658, and FIG. 6C illustrates a detailed view of zirconium oxide recharging flow path 602 on the zirconium oxide side of line 658. The valves, pumps and static mixers illustrated in FIGS. 6B and 6C can allow for inline mixing of the recharging fluids. In FIG. 6A, the zirconium phosphate recharging flow path 601 and/or zirconium oxide recharging flow path 602 can be simultaneously or independently connected to a water source 605, a brine source 606, a disinfectant source 607, and a base source 608. Because recharging of the zirconium phosphate in a zirconium phosphate module 603 can require water, brine, and disinfectant, and because recharging of zirconium oxide in zirconium oxide module 604 can also require water, base, and disinfectant, the water source, 605, the brine source 606, and the disinfectant source 607 can be jointly connected to the zirconium phosphate recharging flow path 601, and the water source 605, the disinfectant source 607, and the base source 608 can be jointly connected to the zirconium oxide recharging flow path 602.

In FIG. 6A, zirconium phosphate recharging flow path 601 and zirconium oxide recharging flow path 602 can mix chemicals in-line to create the recharging solutions. Any one of disinfectant source 607, brine source 606, and base source 608 can contain solutions having concentrations over the concentration of the components to be used in recharging the reusable modules. Water source 605 can dilute the disinfectant, brine, and base from the fluid sources prior to recharging. In FIG. 6B, zirconium phosphate pump 610 can pump disinfectant into the zirconium phosphate module 603 with in-line mixing of concentrated disinfectant from disinfectant source 607 from valve 612 through junctions 660 and 661 and into static mixer 618. Concurrently, zirconium phosphate pump 609 can pump water through junction 659 and valve 613 and into static mixer 618 from water source 605. Alternatively, the concentrated disinfectant and water can be mixed through fluid line mixing at the junction of the two fluid lines. The zirconium phosphate pumps 609 and 610 can pump a disinfectant solution having a specified concentration and composition to disinfect the zirconium phosphate module 603 via valves 612 and 613. The disinfectant solution can flow from static mixer 618 through valve 614 to valve 616 and then a resulting solution can flow into the zirconium phosphate module 603 through zirconium phosphate sorbent module inlet 626. Fluid can exit zirconium phosphate module 603 through zirconium phosphate sorbent module outlet 627 into zirconium phosphate effluent line 630. After disinfection of zirconium oxide module 603, zirconium phosphate pumps 609 and 610 can pump water from water source 605 into zirconium phosphate module 603. For example, zirconium phosphate pump 609 can pump water through valve 613 to zirconium phosphate module 603 while zirconium phosphate pump 610 can pump water through valves 611 and 612 to zirconium phosphate module 603. Alternatively, zirconium phosphate pump 609 can pump water through valves 611, 612, and 613 while zirconium phosphate pump 610 pumps water through valves 611 and 612. During recharging, zirconium phosphate pumps 609 and 610 can pump brine through valve 611 to valve 612 from brine source 606 into static mixer 618. If a concentrated brine solution is being used, zirconium phosphate pumps 609 and/or 610 can pump water from water source 605 to static mixer 618 to dilute the brine solution and generate a brine solution having a proper solute concentration for recharging the zirconium phosphate. After pumping brine through the zirconium phosphate module 603, zirconium phosphate pump 609 can pump water through valves 611, 612 and 613 while zirconium phosphate pump 610 can pump water through valve 611 and 612.

The zirconium phosphate recharging flow path 601 of FIG. 6B can have a heater 624 and heat exchanger 625. One or more heat exchangers and one or more heaters can be used. The brine solution can be heated by the heater 624 upstream of the zirconium phosphate module 603. Heat exchanger 625 can utilize the heat from brine exiting the zirconium phosphate module 603 to heat the incoming brine solution upstream of heater 624 to reduce the burden on heater 624. As described, the zirconium phosphate recharging flow path 601 can also have an optional zirconium phosphate module bypass line 628 fluidly connecting valve 615 in the zirconium phosphate inlet line to valve 617 in the zirconium phosphate effluent line 630. The zirconium phosphate module bypass line 628 can neutralize the zirconium oxide effluent with brine even if the zirconium phosphate module 103 is not being recharged. Zirconium phosphate recharging flow path 601 can have a rinse loop 629 connecting valve 614 upstream of the heater 624 and heat exchanger 625 to valve 616 to bypass heater 624 and heat exchanger 625 to rinse brine out of the zirconium phosphate module 603.

Various sensors can be included in the zirconium phosphate recharging flow path 601 to ensure fluid parameters are within acceptable ranges. In FIG. 6B, conductivity sensor 619 can be placed downstream of static mixer 618 to ensure mixing and specified recharging fluid concentrations. Pressure sensor 620 can measure the fluid pressure and to identify leaks or occlusions. Flow sensor 622 can determine the flow rate of the fluid entering the zirconium phosphate module 603 and control zirconium phosphate pumps 609 and 610. Temperature sensor 621 can determine if the recharging fluid is a proper temperature range upon entering zirconium phosphate module 603 and relay data to a processor (not shown) that can control heater 624. Temperature sensor 623 can determine the temperature of the zirconium phosphate effluent prior to entering heat exchanger 625. Other sensor arrangements, including any number of conductivity, pressure, flow, and temperature sensors can be used.

In FIG. 6C, zirconium oxide pump 632 can pump disinfectant from disinfectant source 607 through valve 634 and into static mixer 638 to disinfect the zirconium oxide module 604 in zirconium oxide recharging flow path 602. Zirconium oxide pump 631 can pump water from water source 605 through valve 635 to static mixer 638 to dilute the disinfectant from disinfectant source 607 to provide in-line mixing of the disinfectant solution. The diluted disinfectant can then be pumped through valve 636 to zirconium oxide sorbent module inlet 643 and into zirconium oxide module 604. Effluent from the zirconium oxide module 604 can exit through zirconium oxide sorbent module outlet 644 and into zirconium oxide effluent line 645. After disinfection, the disinfectant can be rinsed from the zirconium oxide module 604 by pumping water from water source 605 through valve 635 to zirconium oxide module 604 by zirconium oxide pump 631 while zirconium oxide pump 632 pumps water through valves 633 and 634 to zirconium oxide module 604. Alternatively, zirconium oxide pump 631 can pump water through valves 633, 634, and 631, while zirconium oxide pump 632 pumps water through valves 633 and 634. To recharge zirconium oxide module 604, zirconium oxide pump 632 can pump base from base source 608 through valves 633 and 634 through junctions 664 and 665 to static mixer 638. Water from water source 605 can be pumped by zirconium oxide pump 631 through junctions 663 and 665 into static mixer 638 to dilute the base by in-line mixing. Alternatively, the water and base can be mixed through fluid line mixing at the junction of the two fluid lines. Alternatively, the base can be pre-set using specified amounts of base in pre-packaged packets or containers. Diluted base can flow through the zirconium oxide recharging flow path 602 and through zirconium oxide module 604. The zirconium oxide module 604 can be rinsed any numbers of times, as needed, by introducing water from water source 605 to the zirconium oxide module 604. The zirconium oxide recharging flow path 602 can also have a zirconium oxide module bypass line 642 that fluidly connects valve 636 to valve 637 in the zirconium oxide effluent line 645 to bypass zirconium oxide module 604. In this way, zirconium phosphate effluent can be neutralized with a base solution even if the zirconium oxide module 604 is not being recharged. A heater and heat exchanger (not shown) can be positioned in the zirconium oxide recharging flow path 602 to heat fluids prior to entering zirconium oxide module 604. A zirconium oxide rinse loop (not shown) can also be included to bypass the heater and heat exchanger. Similarly, the zirconium oxide recharging flow path 602 can also have sensors for measurement and control over the recharging process. In FIG. 6C, a conductivity sensor 639 can be placed downstream of static mixer 638 to ensure that diluted recharging solutions have a desired concentration. Pressure sensor 640 can detect the pressure in the zirconium oxide recharging flow path 602 to detect leaks or occlusions. Flow sensor 641 can detect the flow rate of fluid in the zirconium oxide recharging flow path 602 and can control zirconium oxide pumps 631 and 632.

As shown in FIG. 6A, the present invention can provide in-line neutralization of the effluent from each of the zirconium phosphate recharging flow path 601 and zirconium oxide recharging flow path 602. The zirconium phosphate effluent line 630 can be fluidly connected to zirconium oxide effluent line 645 at effluent line junction 646 and fluidly connected to drain line 647. As shown in FIGS. 6B and 6C, a static mixer 648 can be positioned at or downstream of the effluent line junction 646 to ensure mixing of the effluents from the zirconium phosphate recharging flow path 601 and zirconium oxide recharging flow path 602. The combined effluent can be passed through the drain line 647 to drain 653, a common waste reservoir (not shown), or separate waste reservoirs. A conductivity sensor 650 as shown in FIG. 6B in zirconium phosphate effluent line 630 and a conductivity sensor 652 as shown in FIG. 6C in zirconium oxide effluent line 645 can determine the composition of the effluents. Flow sensor 649 in zirconium phosphate effluent line 630 of FIG. 6B and flow sensor 651 in zirconium oxide effluent line 645 of FIG. 6C can be used simultaneously or independently to measure the flow rates of each of the effluents. Determining the composition of the effluent fluids as well as the respective flow rates using one or more sensors described can monitor the system function and ensure that the combined effluent in drain line 647 is safe for disposal or storage.

Brine source 606, disinfectant source 607, and base source 608 can have filter 654, filter 655, and filter 656, respectively to remove particulate matter prior to entering zirconium phosphate recharging flow path 601 or zirconium oxide recharging flow path 602. The filters can also act as inline mixers to mix the solutions. Water source 605 can have microbial filter 662 to remove microbes from the water. Brine source 606, disinfectant source 607, and base source 608 can be housed outside of a recharger housing denoted by line 657. The brine solution, disinfectant solution, and base solution can be generated through in-line mixing as described. Alternatively, pre-mixed solutions, concentrates, or infusates can be introduced into brine source 606, disinfectant source 607, and base source 608 and delivered to zirconium phosphate recharging flow path 601 or zirconium oxide recharging flow path 602. For example, the brine solution in brine source 606 can be pre-mixed or provide in pre-packaged amounts in the proper concentrations and introduced into brine source 606, disinfectant source 607, and base source 608.

In-line mixing can provide higher concentrations of solutes, lower fluid volumes required by the system, and physically smaller fluid reservoirs. The fluids should have suitable concentrations for use in the zirconium phosphate recharging flow path 601 or zirconium oxide recharging flow path 602. For example, an initially high source of peracetic acid can be used in a concentration of between 20% and 40%. The zirconium phosphate recharging flow path 601 of FIG. 6B can dilute the peracetic acid or other disinfectant in the disinfectant source by a factor of 20:1 to 40:1 to generate an acidic recharging solution having a concentration between 0.5% and 2%. The initial disinfectant concentration can be any concentration greater than 1%. Similarly, the base solution can be sodium hydroxide having an initial concentration between 14M and 22M. The zirconium oxide recharging flow path 602 of FIG. 6C can dilute the base solution by 18:1 to 22:1 to generate a base solution having a concentration between 0.8 and 1.0M. The initial base solution concentration can be any concentration greater than or equal to 0.5M. The brine solution can also be diluted in-line to generate a brine solution having a proper recharging concentration. The brine source 606 of FIG. 6A can be one or more reservoirs. For example, an acetic acid source, a sodium acetate source and a sodium chloride source can each be connected in place of single brine source 606. Alternatively, an acetic acid source, a base source, and a sodium chloride source can be connected in place of the single brine source 606 with mixing of the base and acetic acid to generate the sodium acetate. The individual components can be added to the zirconium phosphate recharging flow path 601 in the proper ratios to generate the recharging brine.

The chemicals used in the recharging process can be packaged and shipped in any form. The chemicals can be packaged and shipped as solutions, either in proper concentrations for use in recharging or with higher concentrations for use in in-line mixing. In any embodiment, the chemicals may be packaged and shipped in pure form, such as 100% acetic acid or solid sodium chloride, sodium acetate, or sodium hydroxide.

Figure 7:
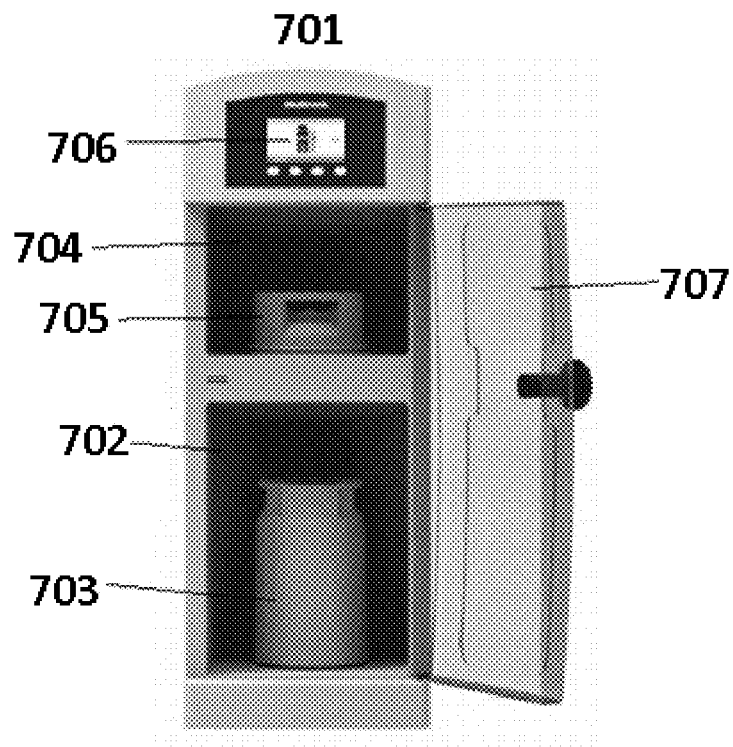
FIG. 7 shows a recharger for recharging zirconium phosphate and zirconium oxide modules.

A recharger can be configured as shown in FIG. 7. The recharger 701 includes a first receiving compartment 702 for receiving a reusable zirconium phosphate module 703 and a second receiving compartment 704 for receiving a zirconium oxide module 705. Fluid connections (not shown in FIG. 7) connect to the top and bottom of the sorbent modules 703 and 705 for passing recharging fluids into, through, and out of the reusable sorbent modules 703 and 705. As described, the recharging fluids replace ions bound to the sorbent materials during dialysis with new ions, recharging the sorbent material within the sorbent modules for reuse in sorbent dialysis. The recharger 701 can be configured to concurrently recharge a zirconium phosphate module 703 and a zirconium oxide module 705, or to independently recharge either a zirconium phosphate module 703 or a zirconium oxide module 705 with neutralization of the effluents of each of the sorbent modules. A user interface 706 is provided to start or control the recharging process by the user. The user interface 706 also provides the status of the recharging process to the user, such as the times of completion of each recharging step, or a time until the recharging process is complete. User interface 706 also provides alert messages if any problems are detected during recharging, such as leaks, occlusions, pump failures, or mismatched chemicals. A door 707 on the recharger 701 controls access to the receiving compartments 702 and 704 during operation. Rechargers with any number of receiving compartments for recharging any number of zirconium oxide and/or zirconium phosphate sorbent modules can be constructed. For example, a recharger with two zirconium phosphate receiving compartments and two zirconium oxide receiving compartments can be similarly constructed. The rechargers can have 1, 2, 3, 4, 5, 6, or more receiving compartments, each capable of receiving zirconium oxide or zirconium phosphate sorbent modules.

Figure 8:
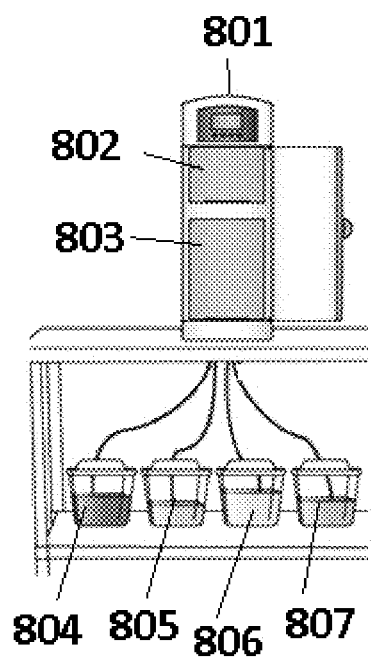
FIG. 8 shows a recharger fluidly connected to external fluid sources.

FIG. 8 illustrates non-limiting embodiment of a recharger set up for recharging zirconium oxide and zirconium phosphate, either concurrently or independently. To recharge the sorbent materials, one or more recharging fluids are passed through the reusable sorbent modules. As shown in FIG. 8, the recharger 801 is fluidly connected to one or more recharging fluid sources, such as water source 804, brine source 805, disinfectant source 806, and base source 807. The recharger has a zirconium phosphate receiving compartment 803 and a zirconium oxide receiving compartment 802. The recharger also has one or more pumps and valves (not shown in FIG. 8) for selectively delivering the recharging fluids from the fluid sources to the reusable modules. As shown in FIG. 8, the recharging fluid sources are housed external to the recharger 801. Alternatively the recharging fluid sources can be housed within the recharger 801. A drain line (not shown) is also connected to the recharger 801 for disposal of waste fluids exiting the reusable modules. The drain line is fluidly connected to a drain, or alternatively, the drain line can be fluidly connected to one or more waste reservoirs for storage and later disposal. The effluents from the zirconium oxide module and zirconium phosphate module are each delivered to the drain line for neutralization of the recharging fluids.

Figure 9:
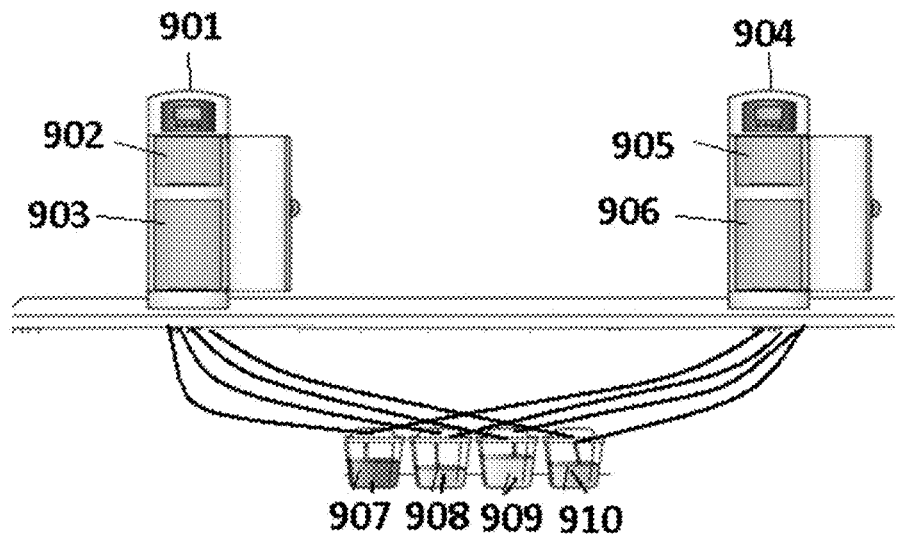
FIG. 9 shows multiple rechargers fluidly connected to a single set of fluid sources.

As illustrated in FIG. 9, multiple rechargers can be chained together and connected to a single set of fluid sources for sharing of infrastructure. A first recharger 901 having a zirconium phosphate receiving compartment 903 and zirconium oxide receiving compartment 902 is fluidly connected to water source 907, brine source 908, disinfectant source 909, and base source 910. A second recharger 904 having a zirconium oxide receiving compartment 905 and zirconium phosphate receiving compartment 906 is also fluidly connected to the same water source 907, brine source 908, disinfectant source 909, and base source 910. Any number of rechargers can be connected to a common set of fluid sources, including 2, 3, 4, 5, 6 or more rechargers, each fluidly connected to a single set of fluid sources and a single set of waste reservoirs. Connecting multiple rechargers to a single set of fluid sources saves space and materials and simplifies recharging multiple sets of reusable modules in a clinic or hospital setting. Each of the rechargers may include a separate drain line and/or separate waste reservoirs, or each recharger may be fluidly connected to a common drain line. The drain line can also be fluidly connected to any one of a drain, a common reservoir, or combinations thereof. Each of the connected rechargers can have separate heaters for heating the brine and/or disinfectant solutions, or centralized heaters can be included, with centralized heating of the shared solutions.

The rechargers can be used in any setting, including a clinic, at home, or in a mobile setting. In any setting, the rechargers can use a water tank or any other source of potable or deionized water. For use in a mobile setting, vans or trucks can carry the rechargers, the disinfectant source, the brine solution, the base solution, and optionally the water, to a location for recharging. For at home use, the brine solution, disinfectant solution, base solution, and optionally the water, may be prepackaged and shipped to a patient. The patient can connect each of the sources to the recharger to allow recharging and reuse of the sorbent modules in dialysis. As described, the rechargers can provide for inline mixing of chemicals, reducing the amount of chemicals required to be moved for use in a mobile setting. Inline mixing of chemicals allows for a smaller amount of concentrated solutions to be moved to a location in a mobile or at home setting, and water from a local water source, such as municipal drinking water, can dilute the disinfectant, base, and/or brine inline. Alternatively, a deionized or purified water source can be provided in a mobile setting. Effluent from the sorbent modules can be collected and neutralized inline for immediate disposal in any drain, or can be collected for later neutralization and disposal offline. The ability to neutralize and dispose of the combined effluents in a drain allow for easier use in an at home or mobile setting, without the need for large waste reservoirs and further treatment.

Figure 10:
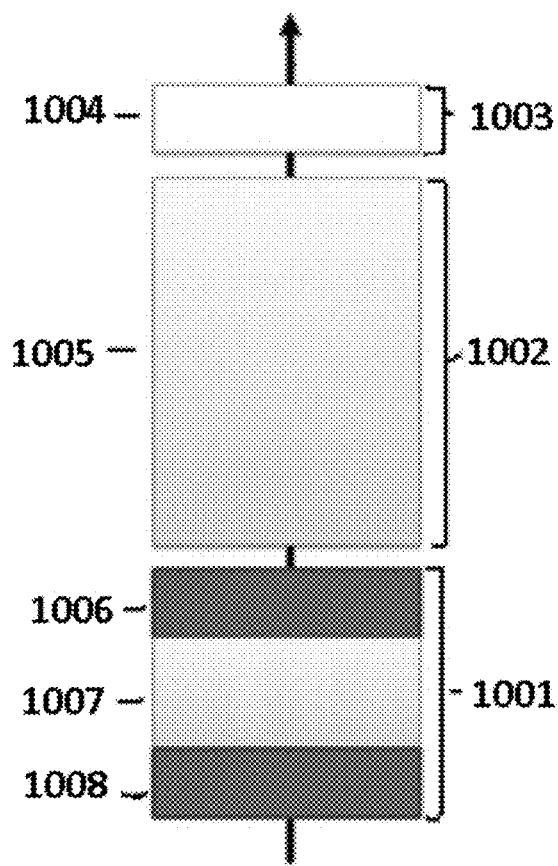
FIG. 10 shows material layers in a module sorbent cartridge including reusable modules.

A non-limiting embodiment of a reusable sorbent cartridge having modules that can be separated and recharged by systems and methods of the present invention is shown in FIG. 10. The sorbent cartridge can be separated into reusable modules to facilitate recharging of one or more sorbent materials. In FIG. 10, the sorbent cartridge has a first sorbent module 1001, a second sorbent module 1002, and a third sorbent module 1003. The first module 1001 can have a layer of activated carbon 1008, a layer of alumina and urease 1007, and a second layer of activated carbon 1006. The activated carbon can remove many non-ionic solutes from the dialysate. The urease catalyzes the conversion of urea in the dialysate into ammonium ions. The alumina can serve as a support for the urease. The second layer of activated carbon 1006 can capture any urease that migrates out of alumina and urease layer 1007 prior to exiting the first module 1001. The first module 1001 can be a single use module, or can be a multiple use module with replenishment of the urease. The second module 1002 can have zirconium phosphate 1005. After dialysis, zirconium phosphate 1005 will contain bound potassium, calcium, magnesium, and ammonium ions, which can be replaced with sodium and hydrogen ions by the recharging process described herein. Third module 1003 can contain zirconium oxide 1004. After use, the zirconium oxide 1004 will contain bound phosphate, fluoride and other anions, which can be replaced with hydroxide anions through the recharging process described herein. The flow direction of flow of dialysate through the sorbent cartridge is shown by the arrow in FIG. 10. The recharging solutions can also flow through the reusable sorbent modules in an opposite direction to improve the efficiency of the recharging process.

Figure 11:
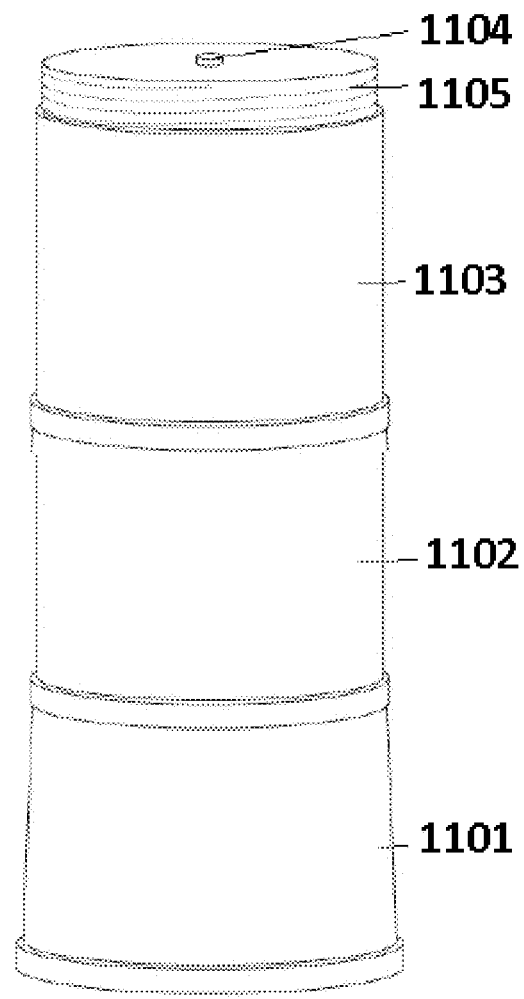
FIG. 11 shows multiple sorbent modules connected together to form a sorbent cartridge.

FIG. 11 illustrates another non-limiting example of a modular sorbent cartridge that can be used in the recharging process described herein. The modular sorbent cartridge can be separated into discrete modules including a first module 1101, a second module 1102, and a third module 1103 connected together to form a sorbent cartridge. The first module 1101 can contain activated carbon, urease, and alumina; the second module 1102 can contain zirconium phosphate; and the third module 1103 can contain zirconium oxide. One of skill in the art will understand that the modular sorbent cartridge illustrated in FIG. 11 is for illustrative purposes only, and modifications to the sorbent cartridge can be made within the scope of the invention. Alternatively, the sorbent modules can be independent with fluid lines connecting each of the sorbent modules for dialysis. During dialysis, dialysate can enter the sorbent cartridge through the bottom of first module 1101, travel through modules 1101, 1102, and 1103, and exit through fluid outlet 1104. The fluid outlet 1104 can connect to the rest of the dialysate flow path. Threaded portion 1105 on module 1103 can be used in connecting modules to each other, to the dialysate flow path, or to the recharger as described herein. The threaded portion 1105 can be included on any of the sorbent modules. Other connection types suitable for secured fluid connection in dialysis known in the art is contemplated by the invention. For example, fluid lines can be clamped directly onto fluid outlet 1104. After dialysis, a user can disconnect the sorbent modules for disposal of single use modules and for recharging of the reusable modules.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A sorbent recharger, comprising:
   at least a first receiving compartment for a first sorbent module; the first receiving compartment having a first sorbent module inlet and a first sorbent module outlet;
   a first inlet line fluidly connected to the first sorbent module inlet;
   a first effluent line fluidly connected to the first sorbent module outlet;
   a disinfectant source, a base source, a water source, and a brine source;
   wherein any one of one of the disinfectant source, base source, water source, brine source, and combinations thereof is fluidly connected to the first inlet line; and
   wherein at least one of the disinfectant source, base source, water source and brine source is fluidly connected to the first effluent line at a common reservoir or a junction with a static mixer at or downstream of the junction.

2. The sorbent recharger of claim 1, wherein the water source, disinfectant source, and brine source are fluidly connected to the first inlet line; and wherein at least the water source and base source are fluidly connected to the first effluent line.

3. The sorbent recharger of claim 1, wherein the water source, disinfectant source, and base source are fluidly connected to the first inlet line; and wherein at least the water source and brine source are fluidly connected to the first effluent line.

4. The sorbent recharger of claim 1, wherein the sorbent recharger comprises a second receiving compartment for a second reusable sorbent module; the second receiving compartment comprising a second sorbent module inlet and a second sorbent module outlet;
   a second inlet line fluidly connected to the second sorbent module inlet;
   a second effluent line fluidly connected to the second sorbent module outlet;
   wherein at least one of the disinfectant source, base source, water source, and brine source is fluidly connected to the second inlet line; and wherein the second effluent line is fluidly connected to the common reservoir or the junction.

5. The sorbent recharger of claim 4, further comprising a conductivity sensor positioned in at least one of the first effluent line and second effluent line.

6. The sorbent recharger of claim 1, further comprising at least a first pump in the first inlet line for pumping fluid from the disinfectant source, base source, water source, and/or brine source to the first sorbent module inlet; and
   at least a second pump for pumping fluid from the disinfectant source, base source, water source, and/or brine source to the junction or common reservoir; and
   a controller for controlling the first pump and second pump.

7. The sorbent recharger of claim 6, wherein the controller is configured to control the first pump to pump fluid from the brine source to the first sorbent module inlet; and to control the second pump to pump fluid from the base source to the junction or common reservoir concurrently.

8. The sorbent recharger of claim 4, further comprising a least one module bypass line, wherein the module bypass line fluidly connects either:
   the first inlet line to the first effluent line; or
   the second inlet line to the second effluent line.

9. The sorbent recharger of claim 4 wherein the first sorbent module inlet is fluidly connectable to the first sorbent module outlet and/or the second sorbent module inlet is fluidly connectable to the second sorbent module outlet.

10. A method, comprising the steps of:
    pumping a brine solution through a first sorbent module containing zirconium phosphate;
    pumping an effluent of the first sorbent module containing zirconium phosphate to a static mixer or common reservoir; and
    concurrently pumping a base solution to the static mixer or common reservoir.

11. The method of claim 10, wherein the step of pumping the base solution to the static mixer or common reservoir comprises the step of pumping the base solution through a second sorbent module, the second sorbent module containing zirconium oxide.

12. The method of claim 10, wherein the step of pumping the base solution to the static mixer or common reservoir comprises the step of pumping the base solution through a module bypass line.

13. The method of claim 10, further comprising the step of pumping fluid from the static mixer or common reservoir to a drain.

14. The method of claim 10, further comprising the step of sensing a conductivity or pH in the effluent of the first sorbent module containing zirconium phosphate with a conductivity sensor, a pH sensor, or combinations thereof; and wherein the step of concurrently pumping a base solution to the static mixer or common reservoir is carried out when the conductivity sensor senses an increase in conductivity, the pH sensor sensing a decrease in pH, or combinations thereof, in the effluent of the sorbent module containing zirconium phosphate.

15. A method comprising the steps of:
    pumping a base solution through a first sorbent module containing zirconium oxide;
    pumping an effluent of the first sorbent module containing zirconium oxide to a static mixer or common reservoir; and
    concurrently pumping a brine solution to the static mixer or common reservoir.

16. The method of claim 15, wherein the step of pumping the brine solution to the static mixer or common reservoir comprises the step of pumping the brine solution through a second sorbent module, the second sorbent module containing zirconium phosphate.

17. The method of claim 15, wherein the step of pumping the brine solution to the static mixer or common reservoir comprises the step of pumping the brine solution through a module bypass line.

18. The method of claim 15, further comprising the step of sensing a conductivity or pH in the effluent of the first sorbent module containing zirconium oxide with a conductivity sensor, a pH sensor, or combinations thereof; and wherein the step of concurrently pumping a brine solution to the static mixer or common reservoir is carried out when the conductivity sensor senses an increase in conductivity, the pH sensor sensing an increase in pH, or combinations thereof, in the effluent of the sorbent module containing zirconium oxide.

19. The system of claim 1, wherein the system comprises the static mixer; and further comprising a pH sensor downstream of the static mixer.

20. The method of claim 10, further comprising:
wherein the step of pumping the effluent of the first sorbent module containing zirconium phosphate to a static mixer or common reservoir comprises pumping the effluent of the first sorbent module containing zirconium phosphate to the static mixer; the step of concurrently pumping a base solution to the static mixer or common reservoir comprises pumping the base solution to the static mixer; and further comprising the steps of determining a pH in a fluid downstream of the static mixer with a sensor; and
pumping the fluid from the static mixer to a drain if the pH of the fluid is between 5 and 9.

* * * * *